United States Patent
Cohen

(10) Patent No.: US 11,602,367 B2
(45) Date of Patent: *Mar. 14, 2023

(54) APPARATUSES AND METHODS FOR CUTTING A TISSUE BRIDGE AND/OR REMOVING A HEART VALVE CLIP OR SUTURE

(71) Applicant: EVALVE, INC., Santa Clara, CA (US)

(72) Inventor: Gideon Cohen, Toronto (CA)

(73) Assignee: EVALVE, INC., Santa Clara, CA (US)

( * ) Notice: Subject to any disclaimer, the term of this patent is extended or adjusted under 35 U.S.C. 154(b) by 401 days.

This patent is subject to a terminal disclaimer.

(21) Appl. No.: 16/853,664

(22) Filed: Apr. 20, 2020

(65) Prior Publication Data
US 2020/0261107 A1     Aug. 20, 2020

Related U.S. Application Data

(63) Continuation of application No. 15/714,692, filed on Sep. 25, 2017, now Pat. No. 10,624,664, which is a
(Continued)

(51) Int. Cl.
*A61B 17/32* (2006.01)
*A61B 17/04* (2006.01)
(Continued)

(52) U.S. Cl.
CPC .. *A61B 17/320016* (2013.01); *A61B 17/0469* (2013.01); *A61B 17/122* (2013.01);
(Continued)

(58) Field of Classification Search
CPC ........ A61B 17/320016; A61B 17/0469; A61B 17/122; A61B 17/1285; A61B 34/20; A61B 2090/376
See application file for complete search history.

(56) References Cited

U.S. PATENT DOCUMENTS

| 3,470,875 A | 10/1969 | Johnson |
| 4,312,337 A | 1/1982 | Donohue |

(Continued)

FOREIGN PATENT DOCUMENTS

| DE | 91 00 873 U1 | 4/1991 |
| FR | 2 705 556 A1 | 12/1994 |

(Continued)

OTHER PUBLICATIONS

U.S. Appl. No. 14/348,527 (U.S. Pat. No. 9,770,256), filed Mar. 28, 2014 (Sep. 26, 2017).
(Continued)

*Primary Examiner* — Phong Son H Dang
(74) *Attorney, Agent, or Firm* — Baker Botts L.L.P.

(57) ABSTRACT

Apparatus for excising and removing a clip or suture joining leaflets of a native heart valve. The apparatus includes an elongate shaft configured for remote access to a native heart valve, the elongate shaft having a proximal end, a distal end, and a lumen defined therein, and a clamp at the distal end of the elongate shaft, the clamp configured to receive a clip or suture joining native leaflet tissue, the clamp including a passageway extending along a length thereof in communication with the lumen. The apparatus further includes a cutter moveable within the passageway to encompass a clip or suture joining native leaflet tissue received within the clamp and cut native leaflet tissue proximate the clip or suture.

21 Claims, 15 Drawing Sheets

Related U.S. Application Data continuation-in-part of application No. 14/348,527, filed as application No. PCT/US2012/058139 on Sep. 28, 2012, now Pat. No. 9,770,256.

(60) Provisional application No. 61/707,856, filed on Sep. 28, 2012, provisional application No. 61/540,156, filed on Sep. 28, 2011.

(51) Int. Cl.

| | | |
|---|---|---|
| *A61B 17/122* | (2006.01) | |
| *A61B 34/20* | (2016.01) | |
| *A61B 17/128* | (2006.01) | |
| A61B 17/00 | (2006.01) | |
| A61B 90/40 | (2016.01) | |
| A61B 17/34 | (2006.01) | |
| A61B 17/3205 | (2006.01) | |
| A61B 17/29 | (2006.01) | |
| A61N 7/00 | (2006.01) | |
| A61B 18/14 | (2006.01) | |
| A61B 90/00 | (2016.01) | |
| A61B 18/00 | (2006.01) | |

(52) U.S. Cl.
CPC .......... *A61B 17/1285* (2013.01); *A61B 34/20* (2016.02); *A61B 17/29* (2013.01); *A61B 17/32053* (2013.01); *A61B 18/1442* (2013.01); *A61B 18/1445* (2013.01); *A61B 18/1482* (2013.01); *A61B 90/40* (2016.02); *A61B 2017/00243* (2013.01); *A61B 2017/00247* (2013.01); *A61B 2017/3435* (2013.01); *A61B 2018/00601* (2013.01); *A61B 2018/1452* (2013.01); *A61B 2034/2051* (2016.02); *A61B 2090/374* (2016.02); *A61B 2090/376* (2016.02); *A61N 7/00* (2013.01)

(56) References Cited

U.S. PATENT DOCUMENTS

| | | | |
|---|---|---|---|
| 5,071,428 A | | 12/1991 | Chin et al. |
| 5,217,460 A | | 6/1993 | Knoepfler |
| 5,238,002 A | * | 8/1993 | Devlin .................. A61B 10/06 606/205 |
| 5,820,630 A | | 10/1998 | Lind |
| 5,908,420 A | | 6/1999 | Parins et al. |
| 6,139,508 A | | 10/2000 | Simpson et al. |
| 6,334,860 B1 | | 1/2002 | Dorn |
| 6,419,640 B1 | | 7/2002 | Taylor |
| 6,932,810 B2 | | 8/2005 | Ryan |
| 7,338,467 B2 | | 3/2008 | Lutter |
| 8,623,077 B2 | | 1/2014 | Cohn |
| 8,821,518 B2 | | 9/2014 | Saliman et al. |
| 9,211,119 B2 | | 12/2015 | Hendricksen et al. |
| 2004/0116951 A1 | | 6/2004 | Rosengart |
| 2005/0159763 A1 | | 7/2005 | Mollenauer et al. |
| 2005/0192633 A1 | | 9/2005 | Montpetit |
| 2006/0184198 A1 | * | 8/2006 | Bales .................. A61B 17/29 606/205 |
| 2008/0009858 A1 | | 1/2008 | Rizvi |
| 2008/0097467 A1 | | 4/2008 | Gruber et al. |
| 2009/0012538 A1 | | 1/2009 | Saliman et al. |
| 2009/0209991 A1 | | 8/2009 | Hinchliffe et al. |
| 2010/0268226 A1 | | 10/2010 | Epp et al. |
| 2011/0009864 A1 | | 1/2011 | Bucciaglia et al. |
| 2011/0184405 A1 | | 7/2011 | Mueller |
| 2011/0238052 A1 | | 9/2011 | Robinson |
| 2012/0022527 A1 | | 1/2012 | Woodruff et al. |
| 2013/0197299 A1 | | 8/2013 | Chin et al. |
| 2014/0228871 A1 | | 8/2014 | Cohen et al. |

FOREIGN PATENT DOCUMENTS

| | | |
|---|---|---|
| WO | WO 95/08292 A1 | 3/1995 |
| WO | WO 99/07295 A1 | 2/1999 |
| WO | WO 2015/008286 A1 | 1/2015 |

OTHER PUBLICATIONS

U.S. Appl. No. 15/714,692 (U.S. Pat. No. 10,624,664), filed Sep. 25, 2017 (Apr. 21, 2020).
U.S. Appl. No. 15/714,692, Mar. 13, 2020 Issue Fee Payment.
U.S. Appl. No. 15/714,692, Dec. 13, 2019 Notice of Allowance.
U.S. Appl. No. 15/714,692, Oct. 29, 2019 Response to Non-Final Office Action.
U.S. Appl. No. 15/714,692, May 31, 2019 Non-Final Office Action.
Dang et al., "Surgical Revision After Percutaneous Mitral Valve Repair With a Clip: Initial Multicenter Experience," Ann Thorac Surg 80:2338-2342 (2005).
International Search Report and Written Opinion dated Jan. 8, 2019 in International Application No. PCT/IB2018/001188.
International Search Report dated Mar. 11, 2013 in International Application No. PCT/US2012/058139.
Rose et al., "Late MitraClip Failure: Removal Technique for Leaflet-Sparing Mitral Valve Repair," Journal of Cardiac Surgery 27:543-545 (2012).
Extended European Search Report dated May 19, 2021 in Application No. EP 18859611.

\* cited by examiner

FIG. 8A
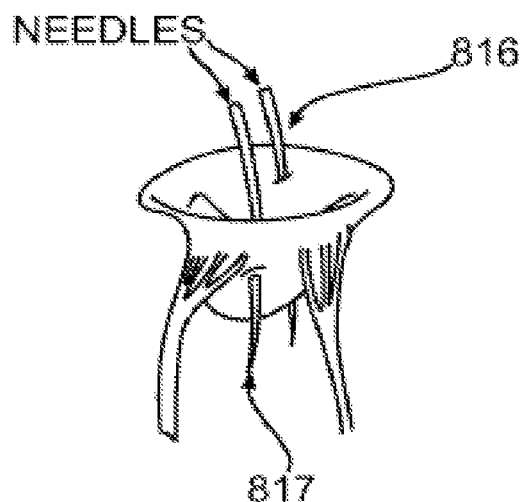
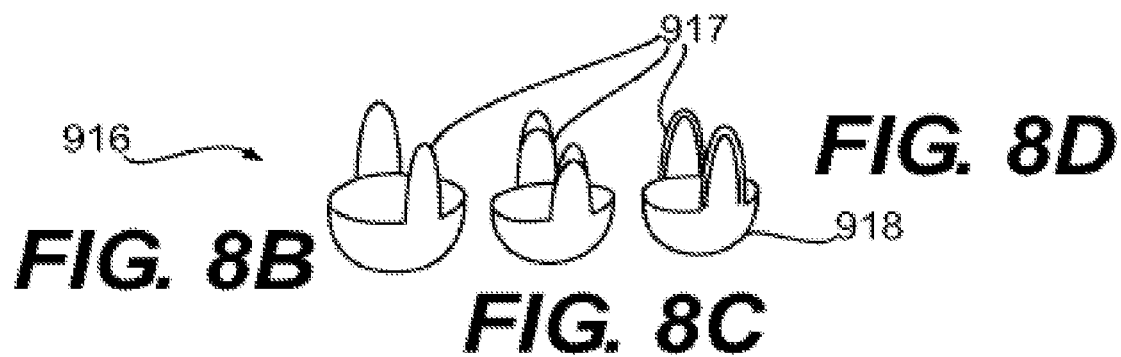
FIG. 8B  FIG. 8C  FIG. 8D
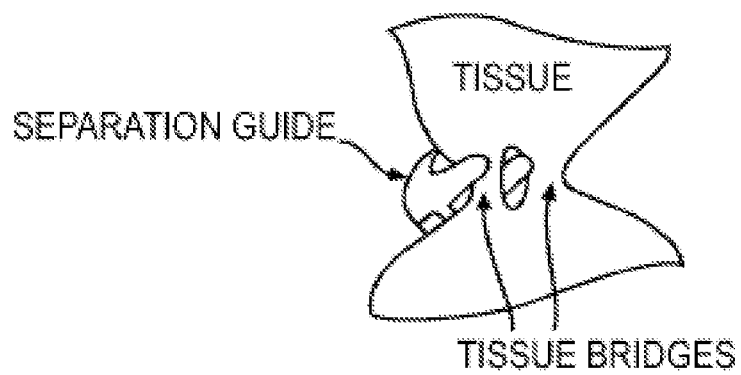
FIG. 8E

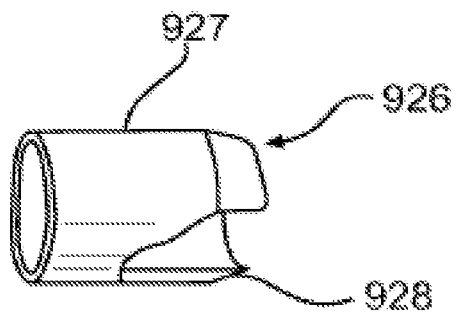
FIG. 9A
FIG. 9B
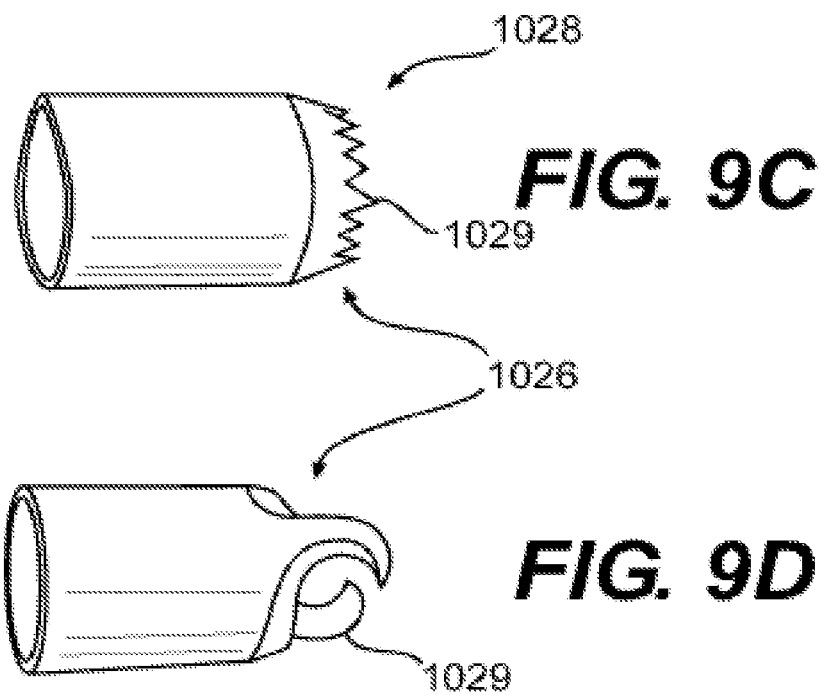
FIG. 9C
FIG. 9D

FIG. 10E 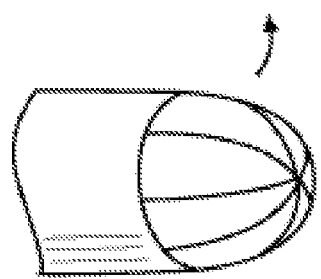 FIG. 10F 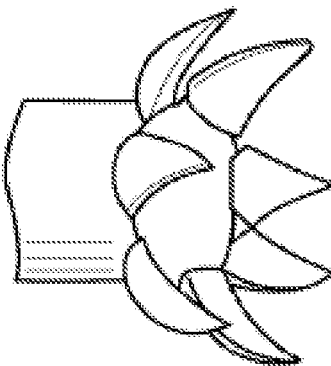
FIG. 10G 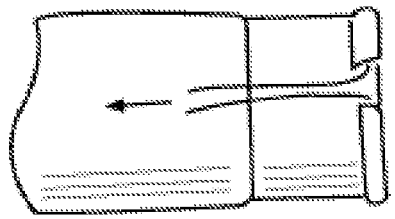 FIG. 10H 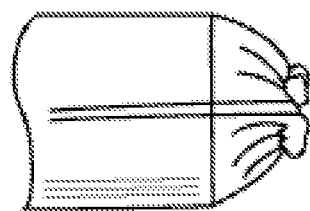
FIG. 10I 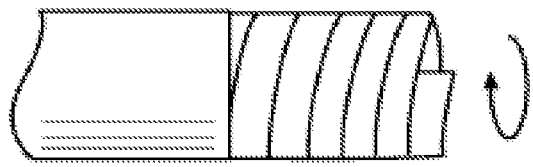 FIG. 10J 
FIG. 10K 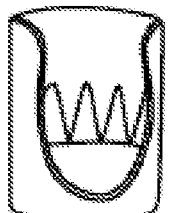 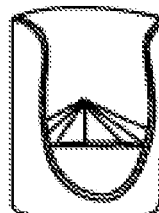 FIG. 10L

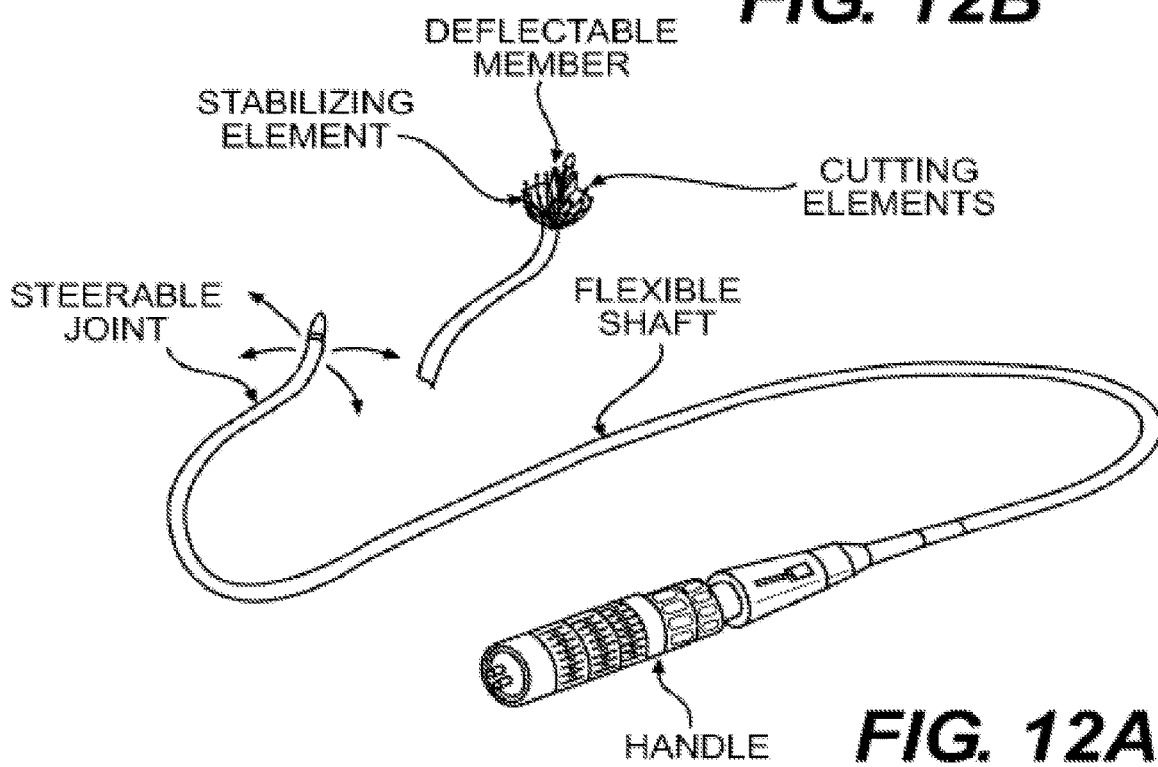
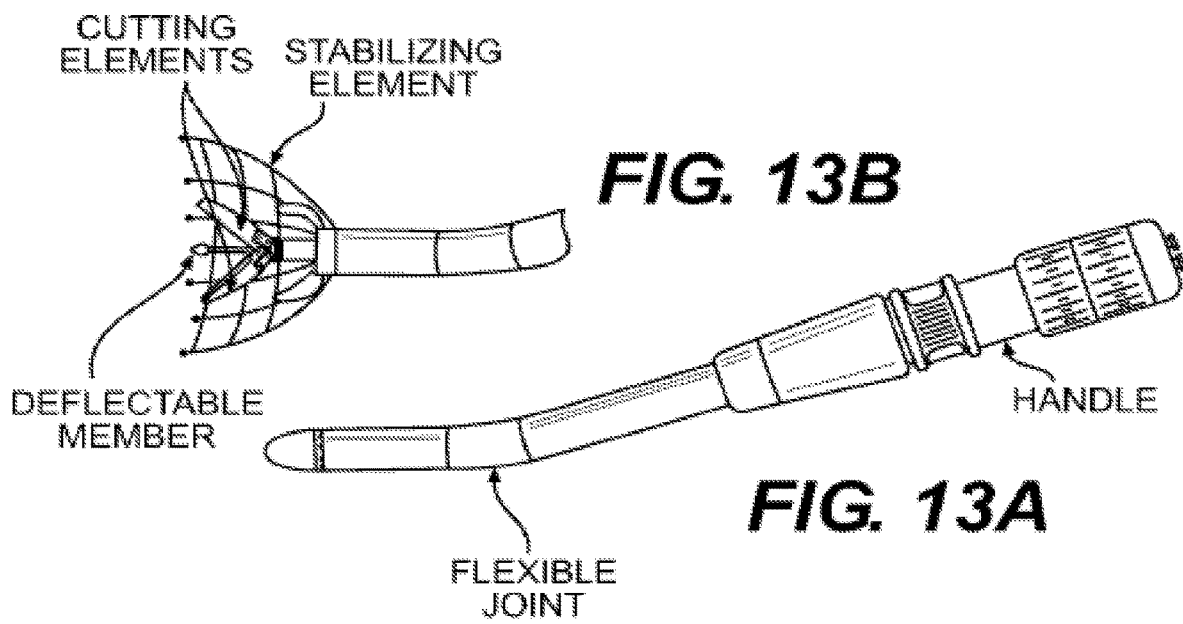

APPARATUSES AND METHODS FOR CUTTING A TISSUE BRIDGE AND/OR REMOVING A HEART VALVE CLIP OR SUTURE

PRIORITY CLAIM

This application is a continuation of U.S. patent application Ser. No. 15/714,692, filed Sep. 25, 2017, which is a continuation-in-part of U.S. patent application Ser. No. 14/348,527, filed Mar. 28, 2014, now U.S. Pat. No. 9,770,256, which is a 371 of PCT/US2012/058139, filed Sep. 28, 2012, which claims priority to U.S. provisional patent Application No. 61/540,156, filed Sep. 28, 2011, and U.S. provisional patent Application No. 61/707,856, filed Sep. 28, 2012, the contents of which are herein incorporated by reference in their entireties.

BACKGROUND

1. Technical Field

The present disclosure relates generally to medical devices and surgical methods for removing a heart valve clip or a suture and tissue from a heart valve.

2. Introduction

There are four valves in the heart. These valves are designed to control the flow of blood through the heart to ensure that the blood flows in only one direction. Valves can fail in one of two ways: either they don't open properly, in which case they become stuck (stenotic), or they don't close properly, in which case they become leaky (regurgitant). One valve in particular, the mitral valve, is prone to leaks. A leak in the mitral valve results in a disorder known as mitral regurgitation. Mitral regurgitation occurs when the leaflets of the heart's mitral valve (anterior and posterior) do not close properly thus causing a leak.

During the heart's contraction, a leak in the mitral valve results in a reversal of blood flow. Blood 'backs up' into the left atrium, thereby decreasing blood flow to the body and increasing congestion of the lungs. Although the heart can usually compensate for this leak in the short term, in the long term, the heart loses its ability to compensate, thus leading to gradual or sudden decompensation. Such decompensation includes enlargement of the heart chamber and weakening of the heart muscle. Flooding of the lungs leads to pulmonary edema and pulmonary hypertension, both of which can lead to permanent damage to the lung tissue. Such changes, if detected and corrected early, may be reversible. If left unchecked, such changes will lead to heart failure and death. As such, a severely leaking mitral valve is almost always an indication for surgical repair.

Until recently, the only method for repairing the mitral valve required open heart surgery. Although such an approach has proven benefits, it comes with a certain degree of risk due to the invasiveness of the operation. As such, the risks involved in the operation are often deemed to be too high for some patients, whom, unfortunately, have to be refused treatment. These patients generally go on to die from their disease.

Recently, a new technology was introduced whereby the mitral valve can be repaired through a catheter without the need for surgery. The procedure, known as the MitraClip™ procedure is based on the "Alfieri" method of mitral valve repair whereby a suture is placed surgically to join together the two (anterior and posterior) leaflets of the mitral valve, thus promoting proper closure. As a minimally invasive, non-surgical alternative, the MitraClip™ procedure enables clipping together of the two leaflets, thus creating a bridge, resulting in a double orifice opening. The bridge may include the clip or suture, which eventually heals over with endothelial tissue. The mitral valve continues to open on both sides of the bridge when the heart relaxes, and closes as required when the heart contracts.

The Alfieri and MitraClip® procedures involve, for example, inserting a catheter through a vein in the groin. The catheter is guided up to the mitral valve under x-ray and ultrasound guidance. Once above the valve, the catheter deploys a clip which joins the anterior and posterior leaflets at the midpoint of the valvular opening. The clip effectively reduces the leak, sometimes eliminating it entirely. The procedure is extremely gentle, and very low risk, even in the most elderly and ill patients. This is currently the only device of its kind on the market.

It is expected that the MitraClip™ will remain a first line therapy for treating mitral regurgitation in selected patients for a number of years. However, new technologies are currently under development which would allow the mitral valve to be replaced entirely through a catheter (Transcatheter Mitral Valve Replacement). Although these technologies are still some time away from clinical application, they may provide an alternative to the Alfieri and MitraClip-™procedures in select patients. Furthermore, in cases where the Alfieri or MitraClip' procedure fails, it is expected that the best option will be mitral valve replacement. Unfortunately, the mitral valve cannot be replaced using transcatheter methods in the presence of a tissue bridge, suture or clip. There is therefore a need for a minimally invasive, catheter based approach to safely remove a tissue bridge, a MitraClip™, a suture, or any other clip device.

There are currently numerous medical devices in use for the removal of tissue from body cavities. However, these devices are not appropriate for use in removing tissue from the heart. Instrumentation for use in heart procedures is very different than instrumentation that may be used in other parts of the body. Firstly, the heart is blood filled, such that no direct visualization can be used, as would be the case with endoscopic devices. Secondly, the heart is mobile and continuously beating, making instrumentation more difficult and potentially hazardous. For these reasons, most cardiac instrumentation involves the use of guidewire technology. This is essential to minimize the risk of cardiac or vascular injury/perforation during manipulation. In contrast, most tissue biopsy devices do not require as exact positioning as do intracardiac devices. Finally, when instrumenting the mitral valve, there is a risk of entanglement of any device with the sub-valvular apparatus which is comprised of a series of cord-like structures which support the valve leaflets, much like a parachute. With guidewire technology, this possibility is mitigated. The ability to steer an apparatus using guidewire technology in the area of the heart valves enables accurate positioning and guidance that is necessary to navigate a clip or suture removing apparatus through two orifices of a double orifice valve.

U.S. Patent Application Publication No. 20080009858A1 discloses a device which is designed to clamp, cauterize, excise and retrieve tissue from the abdomen. This device is not designed to be delivered or applied intravascularly. Moreover, the device could not be utilized intravascularly as electrocautery is ineffective in the presence of a fluid interface. Instead, the device is designed solely for endoscopic use within the abdomen, chest or pelvis. The need for electrocautery as an excision tool is for the purpose of ensuring hemostasis (absence of bleeding following excision). This is not an issue within the heart. Further, the device is not designed to be compatible with guidewire technology.

U.S. Patent Application No. 20060184198A1 discloses a device which is a biopsy forcep designed for use endoscopically. The device consists of jaws which grasp a tissue and a knife which cuts tissue within the jaw. The device is not designed to be used intravascularly and cannot be used with guidewire technology. In addition, the device would not be safe for use within the heart, as the piercing blade is not retractable. In the case of the mitral valve, the blade would be exposed to heart tissues when the jaws are open, thus increasing the risk of injury to normal structures. The cutting mechanism enables for a linear incision within a single plane rather than a circumferential incision, which would be necessary for excision of a mitral tissue bridge.

In some aspects, it may be desirable to provide an apparatus that effectively and safely removes a clip or a suture from the mitral valve to enable placement of a new mitral valve. The device must also be able to safely retrieve the excised clip, suture and/or tissue bridge to prevent intravascular embolization. In some aspects, it may be desirable to provide an apparatus that effectively and safely cuts part of at least one leaflet of the mitral valve to remove the bridge that has been created by the clip or suture. There is a need for such devices that may be deployed through a catheter and which can be used safely and effectively in the heart in proximity to a functioning heart valve.

SUMMARY

The present invention is directed to an apparatus for safely and effectively removing and retrieving a clip, suture, or tissue bridge from a heart valve. The apparatus is operable in association with a guidewire for positioning the device in proximity to a functioning heart valve. The apparatus includes a retractable blade for cutting a tissue bridge which may include a clip or suture, along with a means for removing/retrieving the clip or suture along with the excised tissue from the heart.

In an exemplary embodiment, the apparatus includes a shaft attached to two arm members that secure the clip or suture (along with its tissue bridge) when in a closed position. A retractable blade is located within the shaft and is moveable in the shaft to core out a central portion of a tissue bridge including the clip or suture. A cap is connected to the two arms. The cap is moveable through the arm members in order to enable retrieval of the excised tissue bridge and clip or suture into a chamber within the shaft upon opening of the arms.

According to one aspect of the invention, there is provided an apparatus for excising and removing a clip or suture attached to a heart valve, the clip or suture forming a tissue bridge in said heart valve, the apparatus including: an elongate shaft defining a hollow interior, said shaft having a first end and a second end; a handle attached to the second end of the shaft; an elongate clamping member for engaging and securing said clip or suture, said clamping member being attached to the first end of the shaft, the clamping member having a first end attached to the shaft and a second end, the clamping member including two arm members being moveable between an open position where the arm members are spaced apart and a closed position where the arm members are closed in abutting engagement; the arm members being configured to engage said clip or suture in the closed position, each of said arm members defining a longitudinal passageway; a blade located in said interior of said shaft and being moveable longitudinally in said shaft and in said passageways of said arm members when the arm members are in the closed position, between said second end of the shaft and the second end of said clamping member, the blade being configured to completely encompass said clip or suture and tissue bridge for cutting said tissue bridge when the arm members are engaged to said tissue bridge in said closed position; a clamping member actuating member attached to the handle, said clamping member actuating member being coupled to the clamping member for actuating the arm members between the open and closed positions; a blade actuating member attached to the handle, said blade actuating member being coupled to said blade for actuating the blade from said second end of the shaft to said second end of said clamping member for cutting said tissue bridge, wherein the apparatus defines a port for receiving said guidewire, the apparatus being configured to move along said guidewire in a heart of an individual in order to bring said arm members into proximity to said tissue bridge.

In some aspects, the apparatus also includes a retractable cap attached to at least one of said clamping members, the retractable cap being moveable in said passageways of said arm members when the arm members are in the closed position between the second end of said clamping members and the second end of the shaft for retrieving said clip after cutting of said tissue bridge by said blade; and a cap retracting actuating member located on said handle and coupled to said cap for moving the cap between the second end of said clamping members and the second end of the shaft. According to another aspect of the invention, there is provided an apparatus for cutting a tissue bridge in a heart valve, the apparatus including: two elongate cutting members connected by a rotating joint, the cutting members each having a first end and a second end, each of said cutting members defining an inner cutting surface and being moveable between an open position where the cutting members are spaced apart and a closed position where the cutting members are closed with said cutting surfaces in abutting engagement for cutting said tissue bridge; two gripping members, one of said gripping members being attached to the first end of one of said cutting members for actuating the cutting members between the open and closed positions, wherein the apparatus defines an entry port for a guidewire and an exit port for said guidewire, the apparatus being configured to move along said guidewire in a heart.

According to another aspect of the present invention, there is provided a method for excising and removing a clip or suture attached to a heart valve, the clip or suture forming a tissue bridge in said heart valve, the method including the following steps: making an incision in a heart muscle; introducing a guidewire through said incision into a heart and through a double orifice formed in a heart valve by a clip or suture; forming a purse string suture at said incision for opening and closing said incision; providing an apparatus for excising and removing a clip or suture attached to a heart valve, the clip or suture forming a tissue bridge in said heart valve, the apparatus including: an elongate shaft defining a hollow interior, said shaft having a first end and a second end; a handle attached to the second end of the shaft; an elongate clamping member for engaging and securing said clip or suture, said clamping member being attached to the first end of the shaft, the clamping member having a first end attached to the shaft and a second end, the clamping member including two arm members being moveable between an open position where the arm members are spaced apart and a closed position where the arm members are closed in abutting engagement; the arm members being configured to engage said clip or suture in the closed position, each of said arm members defining a longitudinal passageway; a blade located in said interior of said shaft and being moveable longitudinally in said shaft and in said passageways of said arm members when the arm members are in the closed position, between said second end of the shaft and the second end of said clamping member, the blade being configured to completely encompass said clip or suture and tissue bridge for cutting said tissue bridge when the arm members are engaged to said tissue bridge in said closed position; a retractable cap attached to at least one of said clamping members, the retractable cap being moveable in said passageways of said arm members when the arm members are in the closed position between the second end of said clamping members and the second end of the shaft for retrieving said clip or suture after cutting of said tissue bridge by said blade; a clamping member actuating member attached to the handle, said clamping member actuating member being coupled to the clamping member for actuating the arm members between the open and closed positions; a blade actuating member attached to the handle, said blade actuating member being coupled to said blade for actuating the blade from said second end of the shaft to said second end of said clamping member for cutting said tissue bridge; and a cap retracting actuating member located on said handle and coupled to said cap for moving the cap between the second end of said clamping members and the second end of the shaft, wherein the apparatus defines two ports for receiving said guidewires (one for each orifice), the apparatus being configured to move along said guidewires in a heart of an individual in order to bring said arm members into proximity to said tissue bridge; attaching said apparatus to said guidewires; opening said incision and moving said apparatus along said guidewires into proximity of said tissue bridge; securing said apparatus to said tissue bridge with said clamping member; cutting said tissue bridge with said blade and removing said tissue bridge including said clip or suture with said cap.

Another aspect of this disclosure relates to a method including inserting an instrument into a valve orifice within a human heart, deploying a first member from a first portion of the instrument, wherein the first member is configured over a tissue bridge having an associated clip or suture, deploying a second member from a second portion of the instrument, wherein the second member is configured below the tissue bridge having the associated clip or suture and moving the second member towards the first member, to yield a combined member such that the tissue bridge is cut and the combined member contains the associated clip or suture. The method includes folding the combined member into the instrument and retrieving the instrument from the valve orifice. The combined member stores the clip or suture as well as a cut portion of the tissue bridge. The cutting can occur via sharp edges of the members, a laser configured on a member, or another electromagnetic signal emitted from a member.

Another aspect relates to an instrument including an elongated shaft and a first member configured in the elongated shaft such that the first member can be deployed from a first portion of the instrument, wherein the first member, when deployed, is configured over a tissue bridge within a heart, the tissue bridge having a clip or suture. A second member is configured in the elongated shaft such that the second member can be deployed from a second portion of the elongated shaft, wherein the second member, when deployed, is configured under the tissue bridge within the heart and the clip or suture. The elongated shaft is configured such that the second member, when deployed, can move towards the first member, when deployed, to yield a combined member which receives the tissue bridge and the clip or suture. The elongated shaft then receives the combined member. An emitter of a laser or other electromagnetic signal can be configured on a member, on both members and/or on the elongated shaft such that the tissue bridge can be cut without the need of a sharp member edge. A controller and control a direction of a laser or other emitter to aid in accurate delivery of the signal for cutting the tissue bridge.

BRIEF DESCRIPTION OF THE DRAWINGS

FIGS. 8A-8E illustrate exemplary guiding arrangements;

FIGS. 9A-9H illustrate exemplary cutting arrangement;

FIGS. 10A-10L illustrate exemplary containment arrangements;

FIGS. 12A and 12B illustrate an exemplary apparatus according to the present disclosure;

FIGS. 13A and 13B illustrate an exemplary apparatus according to the present disclosure;

DETAILED DESCRIPTION

Reference will now be made in detail to specific embodiments or features of the disclosure, examples of which are illustrated in the accompanying drawings. Generally, corresponding or similar reference numbers will be used, when possible, throughout the drawings to refer to the same or corresponding parts.

Figure 1:
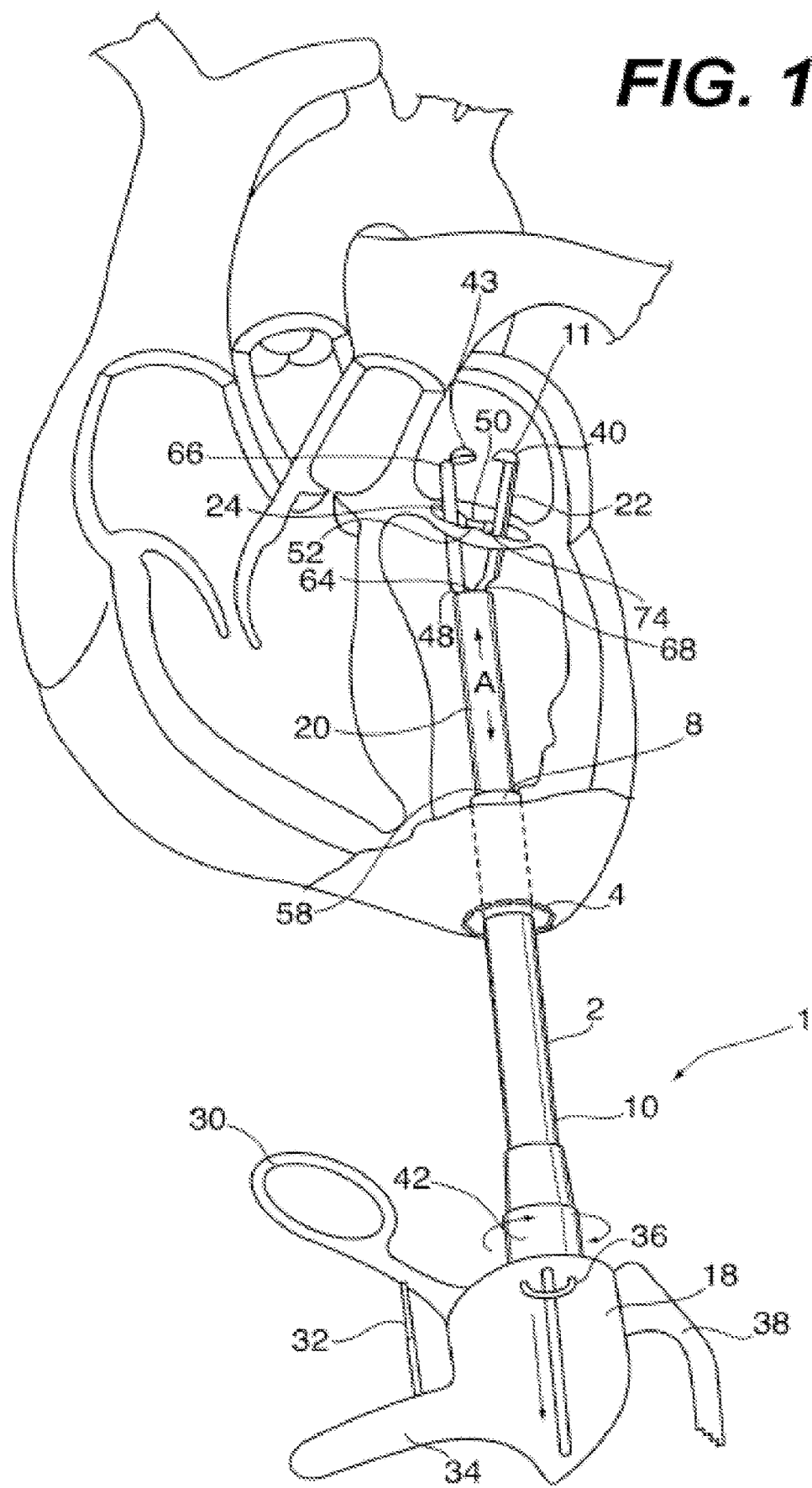
FIG. 1 is a perspective view of an exemplary embodiment of an apparatus according to the present disclosure shown in use in association with a human heart.
Figure 14:
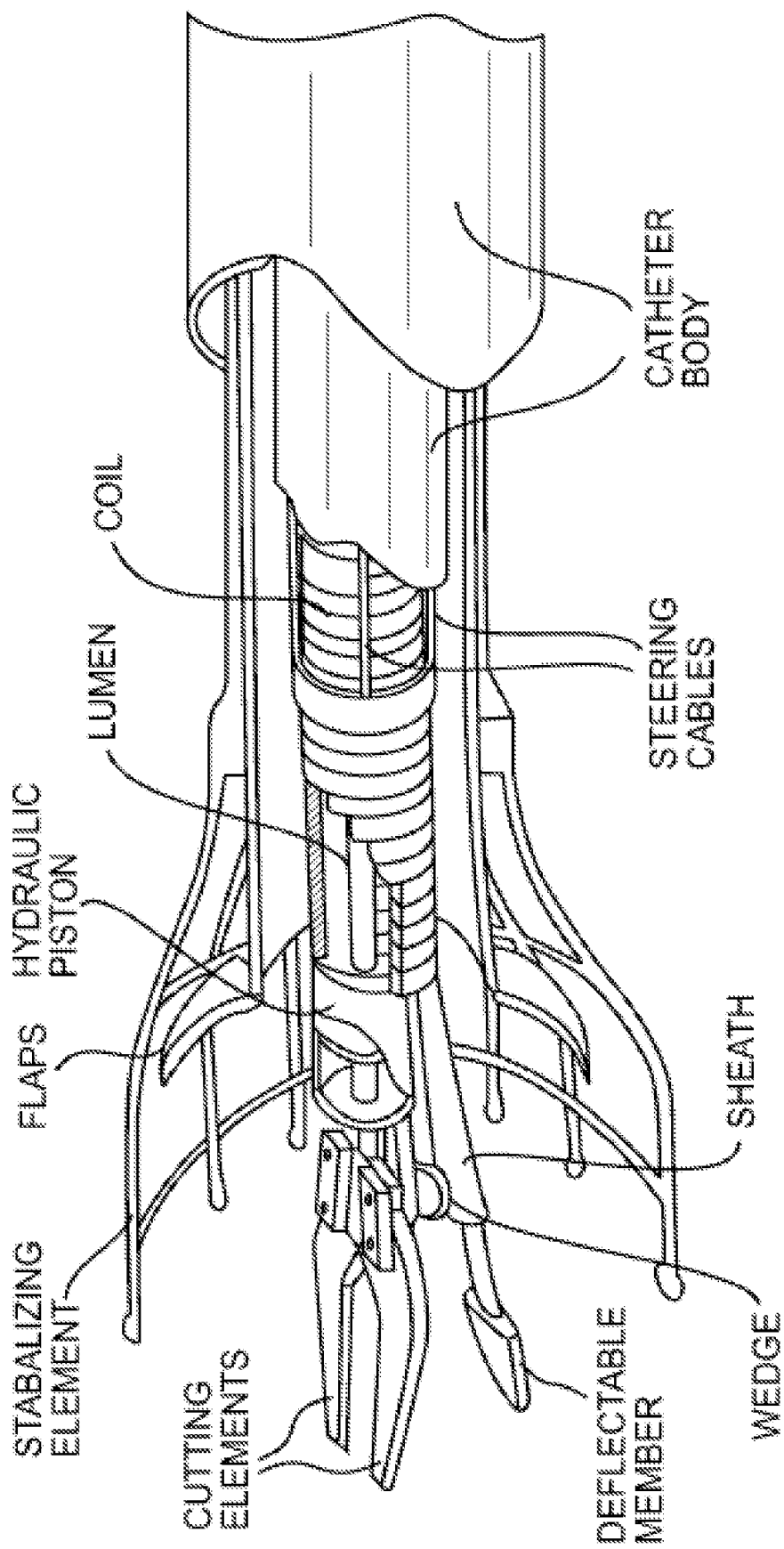
FIG. 14 illustrates an exemplary effective end of the apparatuses of the disclosure.

Referring to FIG. 1, an exemplary apparatus 1 of the present disclosure may be used to remove a tissue bridge 50 including, for example, a clip or a suture that has been secured to the mitral valve of a heart in order to prevent mitral regurgitation. The installation of the clip or suture creates a tissue bridge with a double orifice valvular opening. In some aspects, the clip may be a MitraClip™. Other exemplary apparatuses are illustrated in FIGS. 12-14.

The apparatus 1 includes an elongate hollow shaft 2. The shaft 2 has a first end 8 and a second end 10. The first end 8 of the shaft 2 defines an opening 58. The shaft is hard and rigid and may be constructed, for example, of stainless steel or a synthetic polymer material such as, for example, Pebax, nylon, polyethylene, poly Polysulfone, Polyimide, polycarbonate, Acrylonitrile Butadiene Styrene (ABS), Poly tetra fluoroethylene (PTFE), Polyethylene Terephtalate (PET), or the like.

Figure 3:
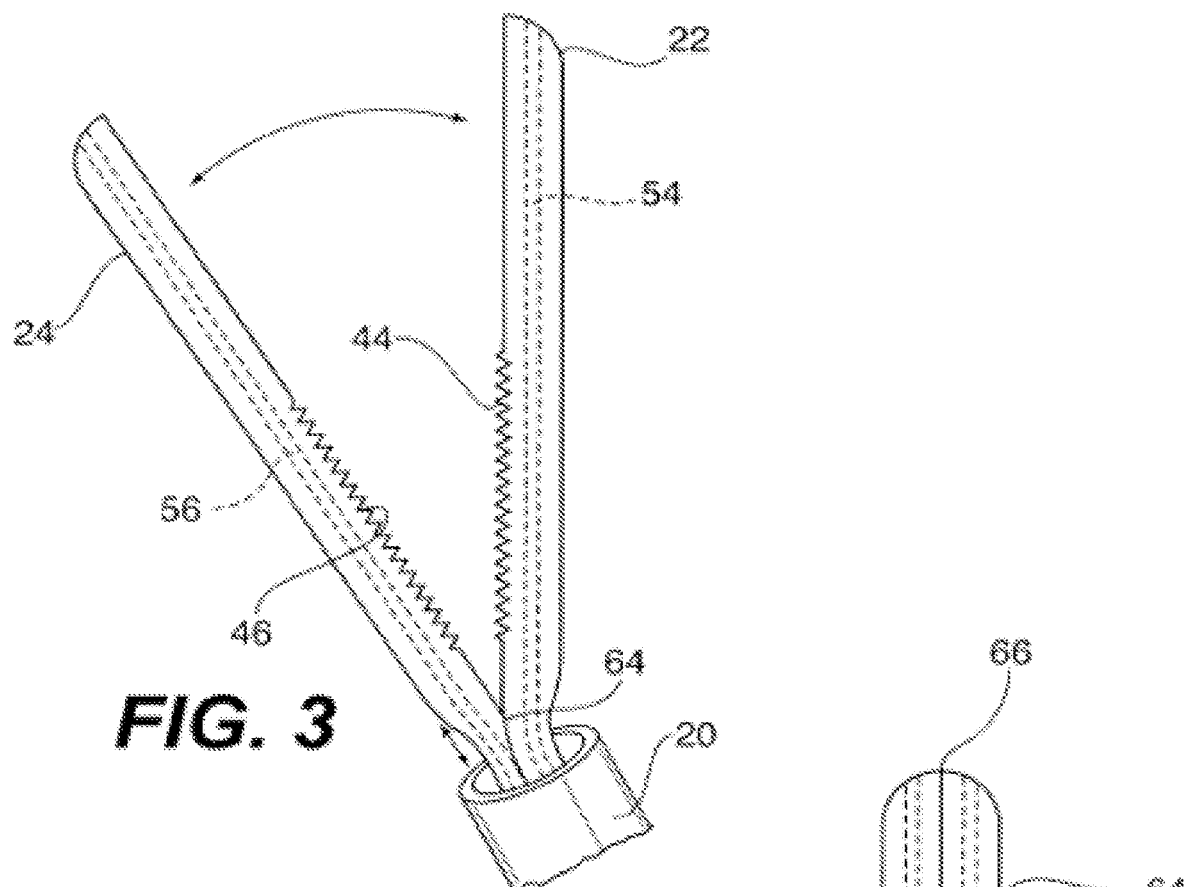
FIG. 3 is a fragment view showing arms of the apparatus in an open position (longitudinal and cross-sectional)
Figure 4:
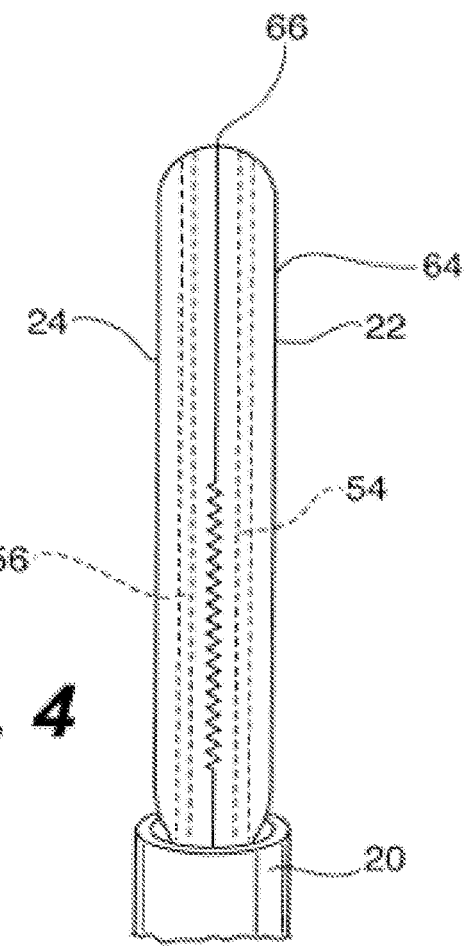
FIG. 4 is a fragment view showing arms of the apparatus in a closed position (longitudinal and cross-sectional)

A distal tube 20 is received in the shaft through the opening 58. The distal tube 20 is disposed in the shaft 2 for telescoping movement therein. The distal tube 20 is hollow and has an open first end 48. A clamping member 64 including a first elongate arm member 22 and a second elongate arm member 24 is received in the open first end 48 of the distal tube 20. The clamping member 64 has a first distal end 66 and a second proximal end 68. As shown in FIGS. 3 and 4, the first arm member 22 defines an elongate passageway 54 formed therein. The second arm member 24 defines an elongate passageway 56 formed therein. The arm members 22, 24 are attached at a bottom end to form a clamp structure. The arm members 22, 24 may each have a jagged section 44 and 46 respectively formed on inner surfaces thereof. The arm members are moveable between an open position as shown in FIG. 3 and a closed position as shown in FIG. 4. In some embodiments, the arm members 22, 24 are biased to the open position by a biasing member. The distal tube 20 is sized and configured such that movement of the distal tube 20 upwardly out of opening 58 of the shaft 2 actuates the arm members 22, 24 to the closed position as the clamping member 64 is received in the distal tube 20. A person skilled in the art will appreciate that other means for actuating the arm members between the open and closed positions may be employed.

Further, it should be appreciated that various gripping arrangements are contemplated as alternatives to the arm members 22, 24 and jagged sections 44, 46. During the excision process, the excised tissue to be removed needs to be properly gripped so that both the cut and the retrieval can be performed effectively. The gripping device should provide a steady interface between the gripping device and the targeted piece. The gripping device might need to come in contact with a variety of surfaces, such as soft, thin floppy tissue, structures with soft mesh-like surfaces, hard nodules covered with soft slippery tissue, hard nodules with metallic protrusions, structures that exhibit spring-back effects when a pressure is applied, surface that indents or gets perforated easily, or any combination of the above. The gripping device will need to maintain contact with such a surface while in operation. It should be appreciated that various mechanisms that can provide the above-mentioned gripping function. These mechanisms take on many shapes and use different methods to achieve the same goal.

For example, gripping arrangement may be configured as pliers. The pliers may include jagged gripping surfaces or small sharp spikes that can easily embed into soft tissue or meshed surfaces. The tip of the pliers' jaws can be tipped with different teeth configurations and serrations, as would be understood by persons of ordinary skill in the art. The pliers can also have various shapes that can curl around obstructions. This is applicable for excisions done on heart valves where the pliers needs to reach through the valve to grip onto something on the other side of the valve. For example, in the case of a MitraClip' excision, it might be desirable to grasp the back side of the clip that is hidden by the tissue bridge. For such applications, the pliers can have horizontal bars or long knobs/teeth that protrude perpendicularly to the jaws of the pliers. These long protrusions can also apply a compressive force that is perpendicular to the primary plane of motion of the pliers, which can help pack the excised tissue into a very compact shape for easy extraction. In some aspects, the pliers can also assume a pointed shape or a cup-like shape with sharpened edge. The pliers can also have more than one pair of jaws, unlike conventional pliers, to ensure uniform gripping from all sides.

Alternatively, the gripping arrangement may include an encapsulation mechanism configured to surround as much of the target tissue and clip or suture from all sides. For example, the encapsulation mechanism may include a Chinese finger trap, which is a mesh-like sleeve configured to be slid over the target tissue. The sleeve is then pulled lengthwise to decrease the diameter of the sleeve, thus seizing the enclosed tissue. In some aspects, a fish traps may be used if the desired tissue/implant has a cylindrical protrusion. The fish trap includes a cylindrical cage with an inverted funnel that can be slid over the protrusion. The edge of the inverted funnel may include prongs that point towards the inside of the cage, which prevent the tissue from slipping out once the latter enters the cage. Additional teeth or serrations can line the surfaces and struts of the inverted funnel and the interior of the cage to provide more gripping power.

According to various alternative aspects, the gripping arrangement may include articulated scoops with an overall shape like a narrow clamshell, wherein the two halves close around any protrusions that emanate from target tissue/implant. The scoops can assume various shapes. Alternatively, the gripping arrangement may include an inverted sleeve or a coil/spiral configured to cooperate with a threaded cylinder. The gripping arrangement may alternatively include suction cups positioned at the tips or sides of end effectors to capture the target tissue/implant; a spiked or barbed cylinder that can retain tissue pushed into the cylinder, for example, via a plunger; or one or more snares configured to capture and retain the target tissue and clip or suture.

Figure 5:
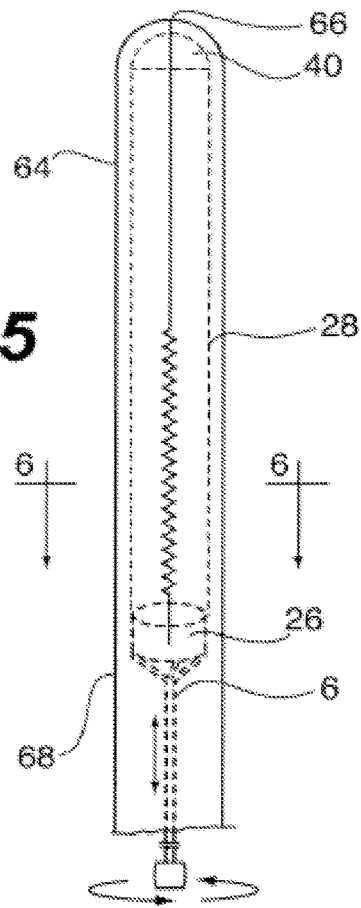
FIG. 5 is a fragment view showing the arms in the closed position (longitudinal)
Figure 6:
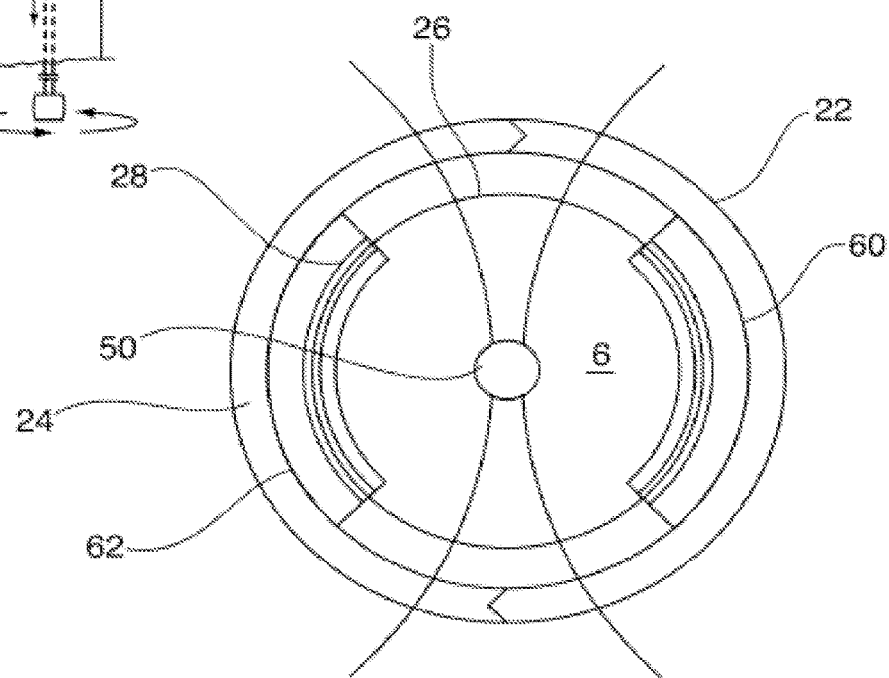
FIG. 6 is a sectional view taken along the lined 6-6 of FIG. 5 including the heart valve outline.

As shown in FIGS. 5 and 6, a blade 26 is located in the interior of the shaft 2. The blade 26 may be retractable. In some aspects, the blade 26 is rotatable and moves rotatably. The blade 26 is disposed in the shaft 2 for movement along the length of the shaft 2. The blade 26 is configured to completely encompass the clip and tissue bridge. In some aspects, the blade 26 is circular in shape, but other shapes are within the scope of the present invention.

Figure 9E:
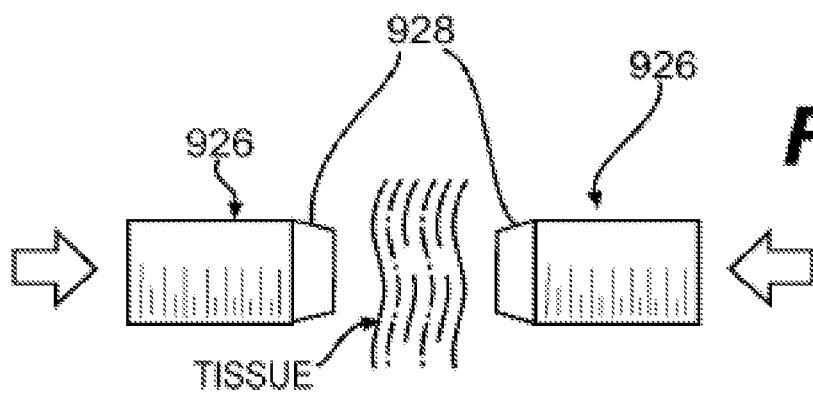

Referring now to FIGS. 9A thru 9H, exemplary embodiments of the blade are illustrated. In some aspects, as shown in FIG. 9A, the blade 926 resembles a biopsy punch. The blade includes a hollow thin-walled metal cylinder 927 in which the edge 928 of one end is sharpened to a razor-like cutting edge.

In some aspects, the only blade movement is a translation along the longitudinal axis of the blade 26 in the direction that moves the cutting edge onto to tissue to be excised. It should be appreciated that the cylindrical blade can have different circumferential shapes including, but not limited to, a circle, an ellipse, a rectangle, a rectangle with rounded corners, etc. The cutting edge 928 can meet the cylindrical wall perpendicularly, or at an angle (FIG. 9B).

According to various aspects, the blade 26 may have two types of movements: the first being a translation along the longitudinal axis of the blade 26 in the direction that moves the cutting edge toward tissue to be excised; and the second being rotation of the cylindrical blade 26 about its longitudinal axis. With this mode of cutting, the cutting edge of the blade imparts on the target tissue both a pushing and a sliding motion. The cylindrical blade in this embodiment will only have a circular circumferential shape.

Referring now to FIG. 9C, a cutting edge 1028 of a cylindrical blade 1026 may be serrated. The serrations 1029 can be uniformly distributed or arranged in a particular manner in which some serrations are of a different size and shape than others. The serrations 1029 can assume the typical triangular shape, or can take other more exotic shapes like that of a sickle (FIG. 9D), spade, or the like.

Figure 9F:
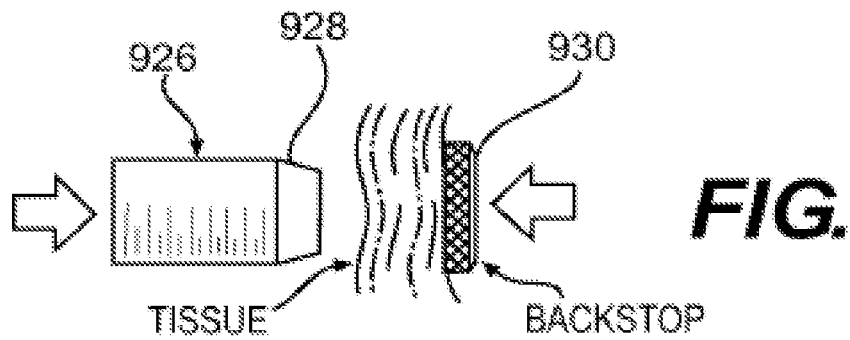
Figure 9H:
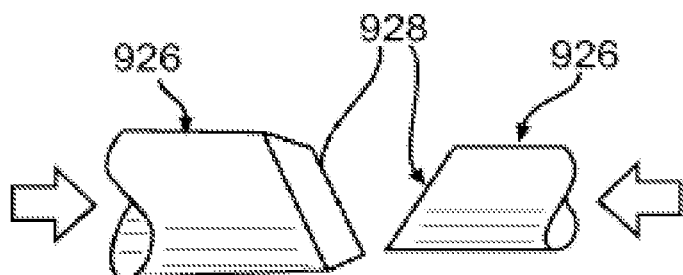
Figure 9G:
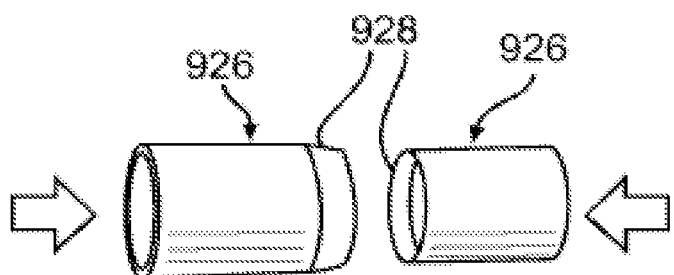

In some aspects, the blade 26 may be the only element of a cutting arrangement, and the one blade is advanced towards the desired tissue throughout the duration of the cutting process. Alternatively, a cutting arrangement 900 may replace the single blade 26. For example, as shown in FIG. 9E, the cutting arrangement 900 may include two blades 926 that can work together acting like jaws, where a target tissue is first positioned between two cylindrical blades 926 having their cutting edges 928 facing each other. Either one or both of the blades 926 can be advanced toward the other until the target tissue is completely cut through. It should be appreciated that the cutting blades 926 can be made such that one is smaller and can be nestled concentrically in the other, as shown in FIGS. 9F and 9G, insuring that the cutting edges 928 can move past each other for a more effective overall cutting motion. According to another aspect, the cutting arrangement may include a blade 926 and a flat backstop 930 that acts as a cutting mat or anvil for the first blade 926 to press against. The target tissue rests on the backstop 930 as the blade 926 is advanced toward the backstop, thus creating a more stable cutting configuration. In any one of the aforementioned embodiments, the blade or blades can also rotate about their longitudinal axes to impart a sliding motion to the cut.

It should be appreciated that a radio-frequency (RF) or an ultrasonic cutting arrangement can be used instead of the mechanical blade. The shape of the RF cutting element or the ultrasonic cutting element can adopt any of the above-described configurations.

Referring again to FIGS. 5 and 6, when the arm members 22, 24 are in the closed position, the hollow shaft, distal tube and passageways 54, 56 define a continuous passageway (not shown) for accommodating movement of the blade 26 from the second end 10 of the shaft 2 to the first end 8 of the shaft 2 and then through the clamping member 64. As shown in FIGS. 5 and 6, a track 28 is may be located in the continuous passageway (not shown) for guiding movement of the blade 26. The track 28 is shown in the clamping member 64 in FIGS. 5 and 6. Blocks 60, 62 may house the tracks.

A cap 40 is attached at the distal end 66 of the clamping member 64. In some aspects, the cap 40 includes two half sections 11, 43. Half section 11 is attached to the first arm member 22 and half section 43 is attached to the second arm member 24. The cap 40 is configured to be moveable in the continuous passageway (not shown) from the first distal end 66 of the clamping member 64 to the first end 8 of the shaft 2 and then to the second end 10 of the shaft 2.

The second end 10 of the shaft 2 may be attached to a handle 18 that includes actuation means for the various functions of the apparatus 1.

A shaft rotating knob 42 may be attached to the shaft 2 at the second end 10 near the handle 18. The knob 42 is coupled to the shaft 2 and rotates the shaft 2. Rotation of the shaft 2 in turn rotates the arm members 22, 24, which are operatively connected to the shaft, to permit ideal orientation of the arm members 22, 24 during operation of the apparatus 1.

A trigger 30 may be attached to the handle 18. A gripping member 34 may be attached to the handle 18 and is positioned to facilitate pulling the trigger through finger action when an operator of the apparatus grips the handle 18. The trigger 30 is connected to a blade actuating member (not shown) located in the shaft. Many different actuating mechanisms known to a person skilled in the art can be coupled to the trigger 30 for moving the blade 26, upon pulling the trigger 30, from the second end 10 of the shaft 2 through the continuous passageway (not shown) to the distal end 66 of the clamping member. In some embodiments, the blade actuating member is comprised of stainless steel. In some aspects, a safety member 32 is positioned between the trigger 30 and the gripping member 34 to prevent actuation of the blade when the apparatus is not in use. The safety member 32 can be removed when the apparatus is put into use.

A cap retracting handle 36 may be attached to the handle 18. The cap retracting handle 36 is moveable on the handle 18 from a first position to a second actuating position. The cap retracting handle 36 is connected to cap retracting actuating member (not shown) located in the shaft 2. Many different cap retracting actuating mechanisms known to a person skilled in the art can be coupled to the handle 36 for moving cap 40 from the distal end 66 of the clamping member through the continuous passageway (not shown) to the second end 10 of the shaft 2. In an exemplary embodiment, the cap retracting actuating member is made of a stainless steel rod.

A lever 38 may be attached to the handle 18. The lever 38 is connected to a clamping member actuating member (not shown) that moves the distal tube 20 upwardly out of the opening 58 at the first end 8 of the shaft 2. The clamping member actuating member is located in the shaft 2. Depression of the lever 38 engages the clamping member actuating member. Many different clamping member actuating mechanisms known to a person skilled in the art can be coupled to the distal tube 20. In some embodiments, the clamping member actuating member is made of a stainless steel rod.

Figure 2:
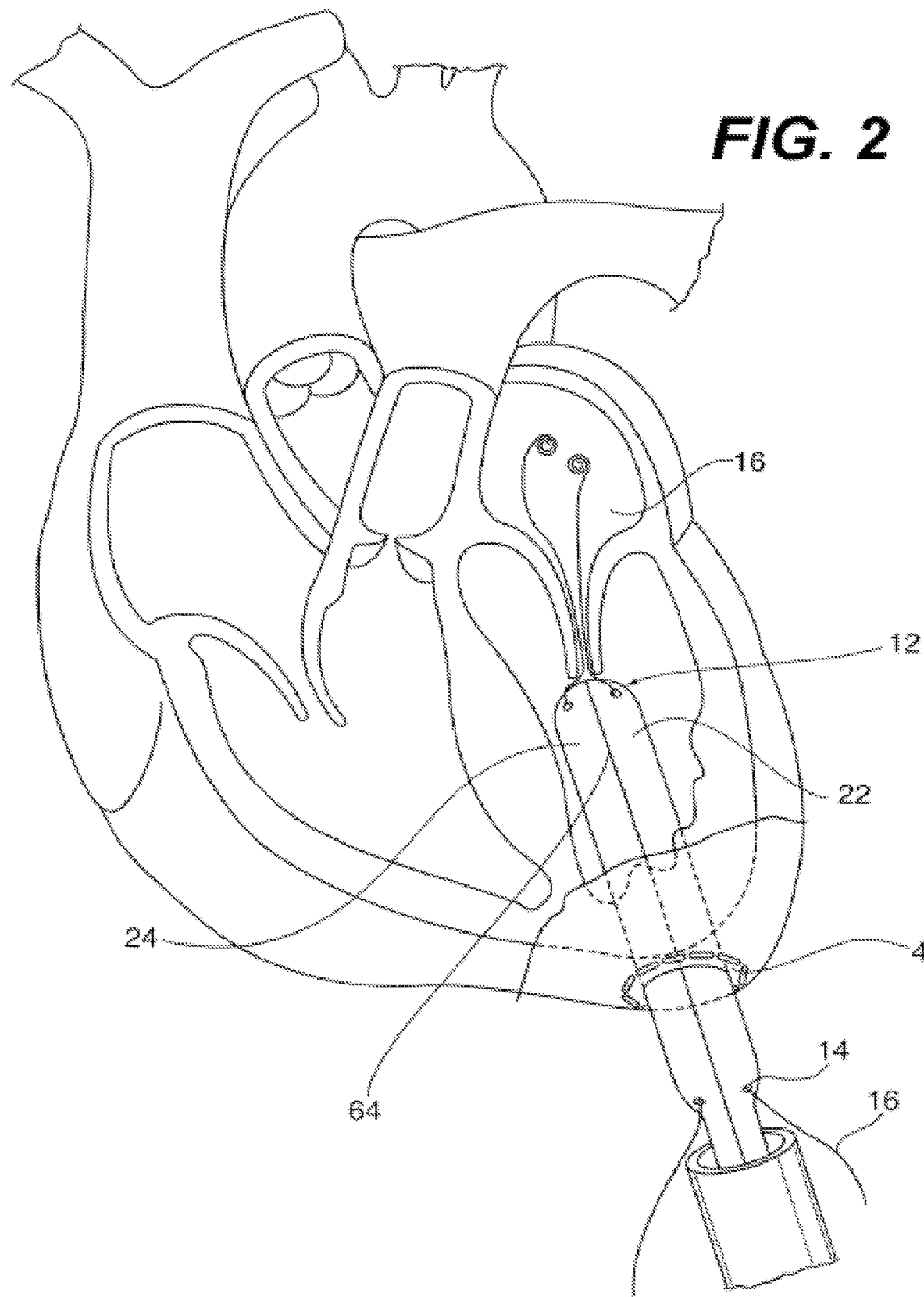
FIG. 2 is a perspective view of the exemplary embodiment showing the apparatus received in the heart.

As shown in FIG. 2, the apparatus 1 defines guidewire entry ports 12 and guidewire exit ports 14 for receiving guidewires 16. The coupling of the apparatus to two guidewires allows for steering of the apparatus in the heart thereby enabling accurate positioning and guidance elements of the apparatus through the two orifices of the double orifice valvular opening. In some aspects, the guidewire entry ports 12 are formed in the distal end 66 of the clamping member and the guidewire exit ports 14 are formed in a proximal end 68 of the clamping member.

Referring now to FIGS. 8A thru 8E, a number of guiding member alternatives to the guidewires 16 are illustrated. FIG. 8A illustrates flexible needles 816, which can be used as guiding members. The needles 816 are long and narrow, similar to guidewires. However, the needles 816 may have sharpened ends 817, which can pierce tissue at target locations, such as mitral valve leaflets. The needles 816 can have different shapes and features, such as barbs and hooks, to facilitate anchoring into the target tissue.

FIGS. 8B-8D illustrate exemplary separation guides 916 that may be used for guiding elements of the apparatus to the target locations. The separation guides 916 may include prongs 917 extended from an end effector 918. The separation guides 916 can create larger separations, for example, in the case of multiple tissue bridges, to thereby allow for better device positioning, as illustrated in FIG. 8E. The prongs 917 may include pointed ends (FIG. 8C) or sharpened edges (FIG. 8D), for example, to cut through any tissue or debris that might be obstructing the orifice between two bridges.

Figure 7:
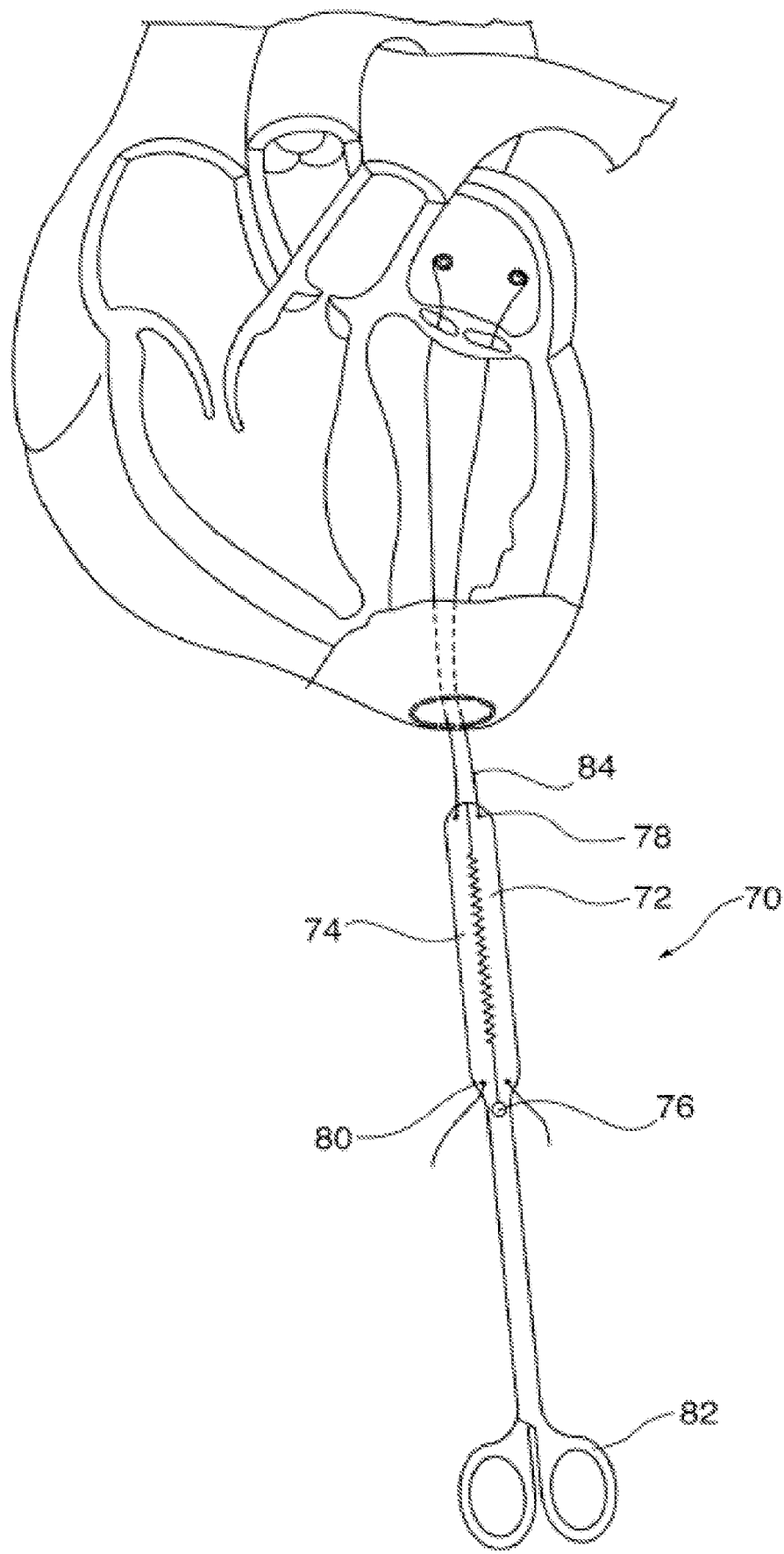
FIG. 7 is a perspective view of an alternate embodiment of an apparatus according to the present disclosure shown in use in association with a human heart.

An alternate embodiment of the present disclosure is shown in FIG. 7. Apparatus 70 is a scissor-like structure including two elongate cutting members 72, 74 connected by a rotating joint 76. Each of the cutting members may have a jagged section. The apparatus has a handle 83 for moving the cutting members 72, 74 between an open position and a closed position for cutting tissue. The apparatus 70 defines guidewire entry ports 78 and guidewire exit ports 80 for receiving guidewires 84.

In operation of the exemplary apparatus 1, an incision is made in the heart muscle to create an entry port for the apparatus 1. For example, the entry port may be at the apex of the heart and the apparatus introduced transapically into the left ventricle. Alternatively, the entry port may be transatrial access, which may provide the advantage of direct entry into the left atrium and avoidance of the tendon chordii associated with the left ventricle. A purse string 4 is employed to open and close the incision as required during the procedure. Two guidewires 16 are introduced transapically into the heart through the incision.

The apparatus 1 is then loaded onto the guidewires 16. The guidewires 16 are received through entry ports 12 and then through exit ports 14. Once the apparatus 1 is loaded onto the guidewires 16, the apparatus may then be moved along the guidewires into the heart under x-ray and ultrasound guidance. In some aspects, the apparatus is applied transapically through a small incision in the chest wall.

Alternatively, an apparatus (FIGS. 12A and 12B) can be introduced by an even less invasive percutaneous approach through a catheter without the need for surgery such as introduction via the femoral artery and consequently entering the heart via the aorta and into the right atrium, traversing the septum into the left atrium, and ultimately in a downward direction to access the mitral valve. The procedure involves inserting a catheter through an artery in the groin (femoral artery). In this embodiment, a separate guide catheter (with a piercing dilator) would be used to cross the inter-atrial septum to enable delivery of the device to a position above the mitral valve. This step would be conducted under x-ray and ultrasound guidance.

In order to accommodate the tortuous vasculature through which the apparatus 1 is introduced to access the heart, as well as the controlled articulation required at the distal end of apparatus 1 in order to steer through the inter-atrial septum and through each heart chamber in order to reach the mitral valve, the shaft of apparatus 1 is desirably made of sufficiently flexible material to navigate such complex a delivery route. As with the alternative transapical and transatrial introduction techniques discussed above, during the transfemoral/transeptal introduction technique the distal end of the apparatus is guided to the mitral valve site via a pair of guidewires which have been previously introduced into the double orifice formed by the tissue bridge at the center of the mitral valve. The remainder of the procedure would be performed similarly to the trans-apical approach, albeit with an 'above-valve' approach rather than a 'below-valve' approach.

The cutting device can be introduced either transfemorally or transapically. The transfemoral form of the device (FIGS. 12A and 12B) will incorporate a long shaft that is flexible throughout its length, while the transapical version (FIGS. 13A and 13B) is mostly rigid with the exception of a possible flexible joint.

Particular to the transfemoral form of the device is the inclusion of a steerable joint that the user can control using the handle in order to steer the device and to guide the cutting effective end to its target.

The effective end of both forms of the device, as shown in FIG. 14, see a set of cutting elements, preferably a pair of shearing blades that is attached to the said steerable joint. Superimposed on the cutting elements is a deflectable member that can be used to help move the target tissue towards the cutting elements, or to nudge the cutting elements into the appropriate target region to perform the cut. The entire effective end can be stabilized within the heart using a stabilizing element. The preferred embodiment of such stabilizing element is in form of a flexible retractable cage, made of either metal or polymer.

One possible way to actuate the cutting elements is to use a linkage system that is connected to a hydraulic piston. The piston is connected to the handle using a lumen through which the user can insert/extract an inflation medium (ex: saline) to activate the piston.

The deflectable member is housed in a sheath. The deflectable member is connected all the way to the handle, and the user can push or pull on the said member to extend or retract it out of or into the sheath. Between the sheath and the piston is a wedge that is also connected to the handle. The user can also push and pull the wedge to increase and decrease the space between the sheath and the piston, thus increasing and decreasing the deflection of the deflectable member.

The piston, the piston lumen, and the sheath is bound together by a torsionally stiff metal coil that runs all the way to the handle. The user can push/pull on the coil to extend/retract the entire effective end into or out of the catheter. The user can also impart a twisting motion into the coil to rotate the effective end around the axis of the catheter shaft.

When the effective end is retracted into the body of catheter, the opening is sealed by a set of closing members, preferably flaps, that makes the tip smooth and atraumatic. The catheter body can be made of one or multiple concentric hollow shafts.

Navigation and positioning for both devices is done by both guidewires and through active steering using steering cables. Near the distal end of the coil, a set of steering cables are laid along the entire length of the coil. The cables are place so that they are diametrically opposing each other, and the distal end of the cables is anchored to the distal end of the coil. The proximal ends are connected to the handle. The user can push/pull on these cables to deflect the tip/effective end of the catheter, thus assisting the user in catheter navigation and positioning of the effective end.

The stabilizing element is also connected to the handle, and the user to push/pull on it to deploy it into the heart, or retract it into the catheter.

Figure 11A:
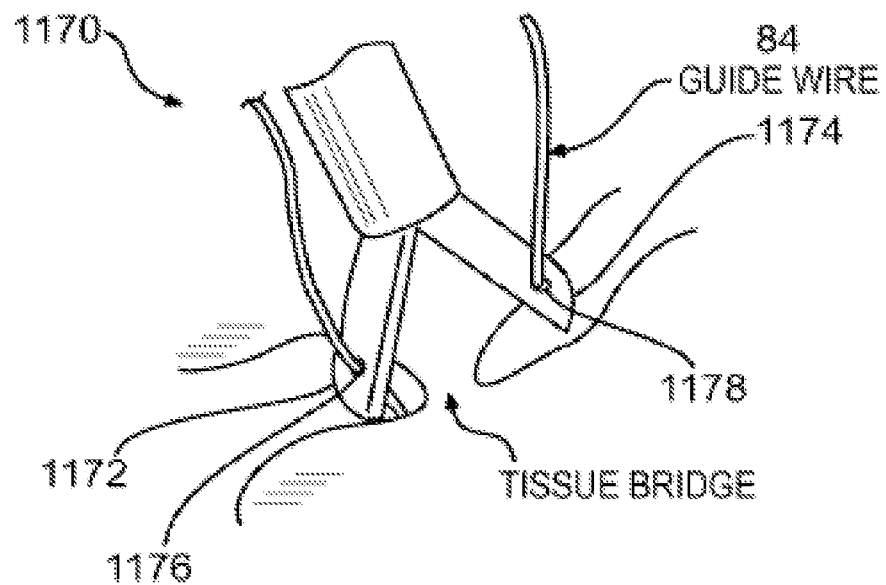
FIGS. 11A and 11B illustrate exemplary cutting arrangements in accordance with the disclosure.

Referring now to FIG. 11A, according to some aspects, a cutting arrangement 1170 may include blades 1172, 1174 having holes 1176, 1178 disposed proximate the tips of the blades 1172, 1174. Guidewires 84 can be threaded through the holes 1176, 1178 to help guide the blades 1172, 1174 to the proper position around the tissue bridge. The active cutting mechanism may be one of tissue shearing between the two blades 1172, 1174 sliding past each other. In order to prevent the blades from cutting into any hard inclusions, such as for example a MitraClip®, the blades of the cutting arrangement must be positioned correctly through imaging. Alternatively, the blades 1172, 1174 of the cutting arrangement can be fitted in oversized rounded sheaths (not shown) that extend beyond the cutting edges of the blades 1172, 1174. In such an embodiment, the holes for receiving the guidewires may be disposed in the sheaths. It should be understood that as the scissors are closed around the tissue bridge, the sheaths will push away any hard inclusions that the blades must avoid. Once the sheaths are closed around the tissue bridge, the blades may be released from the sheath to perform the cut.

It should be appreciated that the cutting arrangement may be configured as any desired cutting mechanism. For example, the cutting arrangement may be configured as a single guillotine-shaped blade arranged to cut from one side of the bridge to the other; a single spear-shaped blade with a pointed tip configured to penetrate the center of the tissue bridge and propagates the cut outwardly towards the sides of the bridge; or a sickle-shaped blade configured to be positioned next to the tissue bridge such that the sharpened inner curve of the blade is aligned with the side of the tissue bridge and arranged to cut the bridge by sliding the blade across the bridge, from one side to the other. In some aspects, the blade may be V-shaped with a sharpened inner curve similar to the sickle. Alternatively, the blade can be U-shaped or can even incorporate a set of hinges to allow for folding into a compact package during introduction. The inner curve is arranged to straddle the tissue bridge from the top or the bottom and can then be thrusted through the bridge to perform the cut.

Figure 11B:
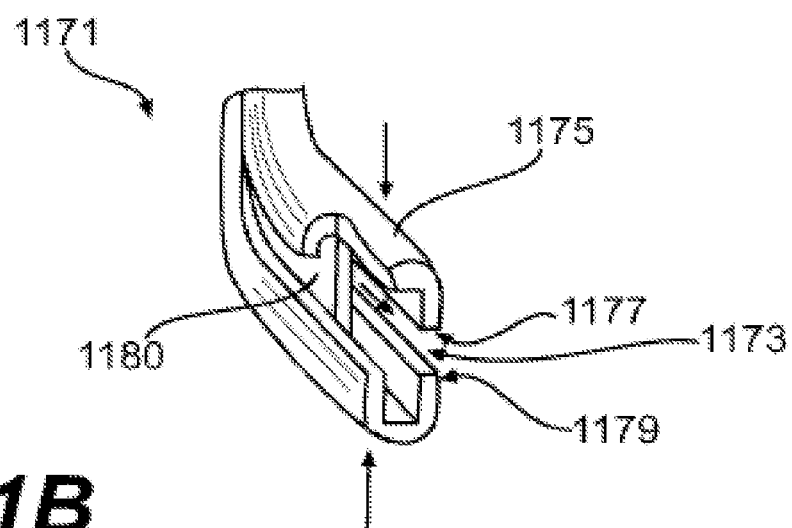

According to some aspects, as shown in FIG. 11B, the cutting arrangement 1171 may include a clamp 1175 configured to secure the tissue bridge from upper and/or lower faces 1177, 1179. The clamp 1175 may include an interior slot 1173 running throughout the entire length of the clamp. When the clamp is engaged onto the tissue bridge, a small blade 1180 housed inside the slot 1173 travels the length of the slot to perform the cut.

It should be appreciated that the cutting arrangement may include circular blade rotatable about a centerpoint, similar to a pizza cutter. A narrow stiff backing plate may be positioned on one side of the tissue bridge, and the circular blade is placed on the opposing side. The plate and the blade are then brought together to sandwich the tissue bridge, and the blade is rolled across the backing plate to perform the cut.

It should be appreciated that a radio-frequency (RF) or an ultrasonic cutting arrangement can be used as the cutting arrangement in any of the aforementioned embodiments. The shape of the RF cutting element or the ultrasonic cutting element can adopt any of the above-described configurations The use of guidewire technology is essential to minimize the risk of cardiac or vascular injury/perforation during manipulation. When instrumenting the mitral valve from the transapical (below-valve) approach, there is a risk of entanglement of any device with the sub-valvular apparatus (a series of cord-like structures which support the valve leaflets, much like a parachute). This risk is reduced by use of guidewire technology, and by the steerable nature of the apparatus, which enables accurate positioning and guidance of the arm members through the two orifices of the double orifice valve. The positioning of the guidewires 16 in the heart is shown in FIG. 2.

The arm members 22, 24 can then be applied in the closed position to enable delivery of the apparatus into the cardiac chamber, i.e., the left ventricle. Lever 38 is depressed to a closed position where it is flush with the handle 18. The clamping actuating member is engaged causing the distal tube 20 to advance. This approximates the arm members 22, 24 to the closed position enabling the apparatus to be guided and steered into the heart chamber. Once there is confirmation via x-ray and/or ultrasound guidance that the apparatus 1 is completely within the heart, the lever is lifted thereby disengaging the clamping member actuating member causing the distal tube 20 to retract. This causes the arm members 22, 24 to move to the open position. The arm members are then guided along the previously positioned guidewires through the valve orifices 74 until the arm members 22, 24s straddle the tissue bridge 50.

As shown in FIG. 1, each arm member 22, 24 is in a separate orifice 74 divided by the tissue bridge 50 with the portion of the tissue bridge 50 having the clip or suture between the two arm members 22, 24. The positioning of the arm members 22, 24 may be adjusted by rotating the shaft 2 with the shaft rotating knob 42. In some aspects, the jagged portion 44, 46 of each arm member 22, 24 is positioned to engage the tissue bridge. Once the apparatus is positioned appropriately across the mitral valve, the guidewires can be removed to minimize the risk of guidewire related injury. The lever 38 is then closed to engage the clamping member actuating member thereby moving the distal tube upwardly out of the opening 58 and closing the arm members onto the portion of the tissue bridge 50 containing the clip or suture. The jagged portion 44, 46 of the arm members 22, 24 ensures adequate apposition of the arm members 22, 24 through the tissue when closed.

Once the tissue bridge 50, including the clip or suture, is secured by the arm members 22, 24, and complete inclusion within the closed arms is confirmed (via x-ray guidance), the blade 26 is advanced along the tracks 28 in the shaft 2 upwardly toward the tissue bridge 50. In order to effect this motion, the safety 32 is released and the trigger 30 is pulled thereby actuating the blade actuating member which actuates the blade 26 up the shaft 2 toward the arm members 22, 24. The blade is then actuated through the passageways 54, 56 in the arm members. The blade 26 is configured in a circular manner, such that it has a cutting surface that completely encompasses the clip or suture and tissue bridge 50. As the blade 26 moves upwardly through the passageways in the arm members 22, 24, it cuts the tissue bridge 50 containing the clip or suture, thereby detaching the clip or suture along with its tissue bridge from the mitral valve.

In order to retrieve the tissue that has been cut away and the clip, prior to opening and disengagement of the arms, the cap 40 is retracted from the distal end 66 of the clamping member 64 to the second end of the shaft 10 along the same path as the blade 26. The cap 40 therefore moves the tissue, clip or suture, and blade 26 downwardly along the shaft 2 to the second end 10 of the shaft 2. This action is accomplished by pulling down on the cap retrieving handle thereby actuating the cap retracting actuating member. The tissue and mitral clip or suture are then safely lodged within the base of the apparatus at the second end 10 of the shaft 2. For precautionary purposes, the cap 40 may remain within the base of the apparatus 1 and is not returned to its original position.

At this stage, the actuating lever 38 is lifted thereby disengaging the clamping member actuating member causing the distal tube 20 to retract. This causes the arm members 22, 24 to move to the open position. This maneuver ensures that there is no remaining valvular tissue caught within the arms of the device prior to removal from the heart. While in the open position, the apparatus is retracted such that the arms lie beneath the valve. Once free of the valvular tissue, the arms are carefully closed to facilitate removal of the device from the cardiac chamber. Care is taken to ensure that no cordal structures are caught within the closed arms. The remaining incision is then closed tying down on the previously placed purse-string suture 4.

It should be appreciated that various containment mechanisms are contemplated as alternatives to cap 40. For example, referring again to FIGS. 9E thru 9H, the blade 926 may cooperate with the backstop or a second blade to act as a containment mechanism for excise tissue. In some aspects, the blade may be locked into place relative to the backstop or second blade throughout the remainder of the procedure after excising tissue and the clip or suture.

Figure 10A:
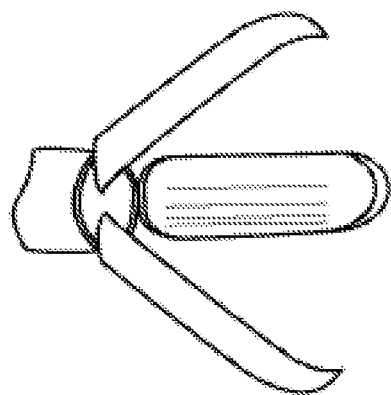
Figure 10B:
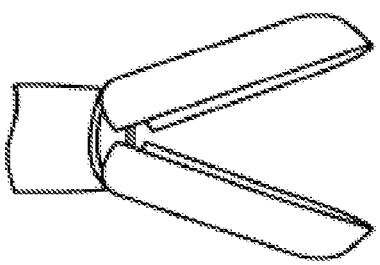

In an alternate embodiment, as shown in FIGS. 10A and 10B, a multi-segmented cylindrical container can be closed over the entire cutting assembly to enclose the excised tissue. The cylindrical container has one end sealed, then cut into multiple sectors with the cuts all originating from one point of the sealed end and running down the length of the cylinder. These sectors can open up like petals of a flower, and then close up around a target.

Figure 10C:
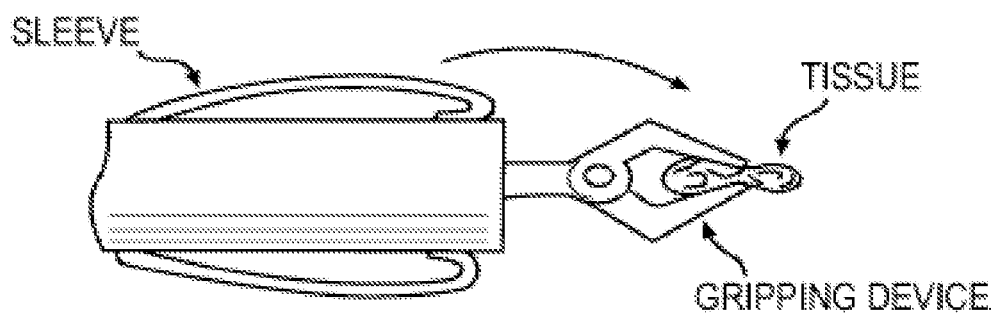
Figure 10D:
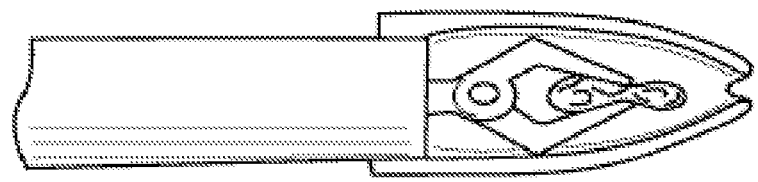

In yet another alternate embodiment, illustrated in FIGS. 10C and 10D, excised target tissue and a clip or suture may be tightly held by the distal end of a gripping device. A flexible, stretchable sleeve can be mounted a priori onto the gripping device such that the entire distal end of the gripping device is entirely covered by the sleeve. The sleeve extends beyond the distal end of the gripping device. The distal end of the sleeve can be shaped such that the distal opening of the sleeve is very small. The proximal end of the sleeve is fixed and/or sealed onto the gripping device. The sleeve can be pulled back and inverted. Once the excised tissue is captured by the gripping device, the sleeve can be folded forward to hide and protect the catch.

According to another embodiment, as illustrated in FIGS. 10E and 10F, a cylindrical container may include a dome sealing the distal end. The dome is split into slices that originate radially from a point on the dome. The slices meet the cylindrical wall at joints that allow the slices to fold backwards to expose the opening of the cylinder. The slices can be powered or passive. A piece of excised tissue can be retrieved by a gripping device housed inside this container, which is then retracted and sealed into the container.

In another embodiment, shown in FIGS. 10G and 10H, a cylindrical container has a soft membrane attached to its distal end, with a drawstring threaded inside. When a gripping device holding the piece of excised tissue is retracted into the cylinder, the drawstring is pulled to seal the cylinder.

According to yet another embodiment, illustrated in FIGS. 10I and 10J, a cylindrical container has a flexible coil attached at its distal end. The coil is optimally made from a thin but wide ribbon of material, and is shaped in such a way that the coil acts as an extension of the cylinder, conserving both its inner and outer diameters. When a gripping device holding the piece of excised tissue is retracted into the cylinder, the distal end of the coil is induced to twist. This twisting motion will in turn tighten the radius of each of the coil's loops, thus making the coil act like a cap. It should be understood that in some aspects the ribbon may be a shape memory material have the tightened configuration in an unconstrained configuration. The ribbon can be constrained from tightening and then released to the unconstrained configuration upon retraction of the gripping device into the cylinder. It should be appreciated that other known arrangements for expanding and collapsing the ribbon of materials are contemplated by this disclosure.

In still another embodiment, as shown in FIGS. 10K and 10L, when a cylindrical container is used, one or more rings of small tabs can be attached to the distal interior of the cylinder. Each tab can be different, however it may be optimal for them to be triangular is shape. Each tab is installed inside the cylinder in such a way that the peak of the triangle is pointing away from the cutting edge. The tabs are in some aspects flexible in nature. When the gripping device is retracted into the distal end of the cylinder while holding onto the excised tissue, the peaks of the tabs can be raised to seal the tube's entrance. The peaks can be raised manually or automatically.

In the alternate embodiment shown in FIG. 7, the apparatus is introduced into the heart in the same manner as with the exemplary embodiments discussed above. This embodiment is designed for use in the chronic scenario i.e. in patients who have had the MitraClip' in place for months or years, in which case the endothelial tissue has overgrown the implanted clip, and in which case cutting of the tissue bridge would not lead to clip dislodgement/embolization, as the clip would have already been incorporated into the valve leaflet due to tissue overgrowth. In such cases, clip retrieval is not necessary. This design is scissor-like and includes a lengthy and completely flexible snake-like handle, where the scissor tips can be guided by guidewire technology through the two orifices of the heart valve. The cutting members are employed to simply cut out the tissue bridge.

Figure 15:
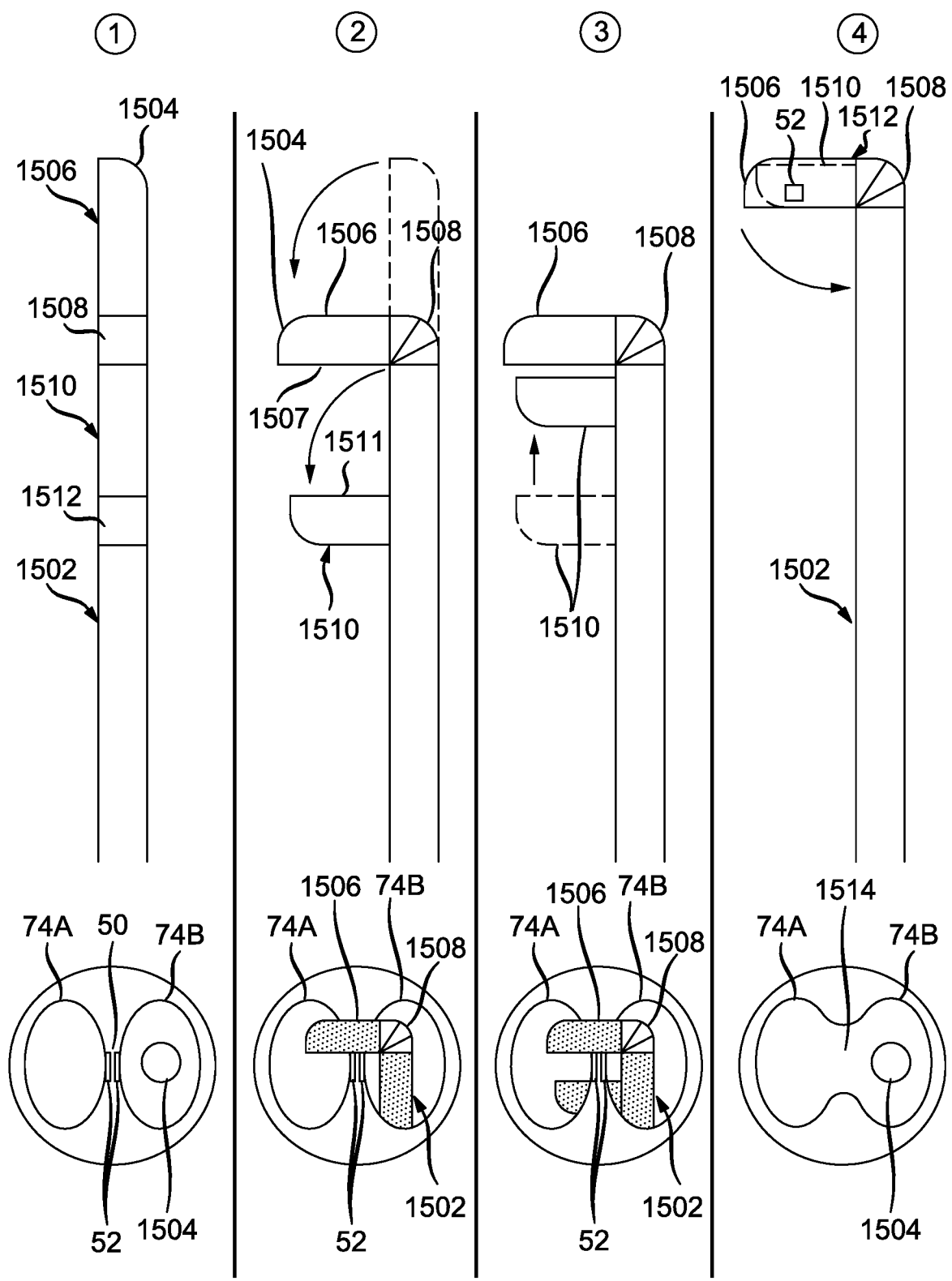
FIG. 15 illustrates another embodiment of this disclosure.

FIG. 15 illustrates another example instrument disclosed herein. The instrument generally referenced as feature 1502 includes several components. FIG. 15 illustrates four stages of use of the instrument. The purpose of this structure is to enable the instrument 1502 to be introduced into a valve orifice such that it can be deployed to straddle a tissue bridge 50 that divides a first valve orifice 74 *a* and a second valve orifice 74B. At stage 1 shown in FIG. 15, a top portion of the instrument 1504 is shown from a top view is being inserted into the second valve orifice 74B. At this stage, the instrument 1502 is in the extended configuration. The tissue bridge 50 can have a clipboard suture 52 positioned thereon. The purpose of the instrument 1502 is to be inserted into the valve orifice 74B, and to be deployed, such that members can envelop the clipboard suture 52, retrieve the clip or suture 52, as well as cut the tissue bridge 50. Walking through steps 1-4 of FIG. 15 will illustrate the process as well as the operation of the instrument 1502.

Once the instrument 1502 is positioned within the valve orifice 74B, a first member 1506 can be deployed by rotating, via an elbow 1508, the first member 1506 into a first position. This movement is shown in step 2 of FIG. 15. The structural mechanism for performing this elbow operation can vary as long as it performs the function shown in step 2. A second member 1510 is also moved to the position shown in step 2 by rotating the member 1510 from a position within a tubular structure of instrument 1502. A mechanical hinge or other structure 1512 can be utilized to rotate the second member 1510 into the position shown in step 2. Not shown in FIG. 15 are the structures utilized to control the movement and positioning of the first member 1506 and the second movement member 1510. Wires, electronic means, wireless communication, mechanical controls, or any other combination of electronic and mechanical structures can be utilized to position the first member 1506 and the second member 1510 as shown. All such structures as would be known to one of skill the art are considered within the scope of this disclosure.

A bottom portion of step 2 in FIG. 15 shows the instrument 1502 inserted into the second valve orifice 74 and being configured such that the first member 1506 is positioned via the rotation by the elbow 1508 to be over the clips or sutures 52 and over the tissue bridge 50.

Another aspect of the structure and configuration of the first member 1506 and the second member 1510 is that an underside 1507 of member 1506 is configured such that a cavity exists which can receive the second member 1510. The second member 1510 also has a cavity 1511 configured therein. The purpose of these cavities is shown in step 3. In this step, the second member 1510 slides upward from a first position to a second position, as shown in step 3. The bottom portion of step 3 illustrates how the movement of the second member 1510 towards the first member 1506 can ultimately envelop the clip or suture 52 configured with the tissue bridge 50. A portion 1513 of instrument 1502 enables the sliding of the member 1510. The movement of the second member 1510 will continue until the tissue bridge 50 is cut and the clip or suture 52 associated with the tissue bridge 50 is contained within the combined first member 1506 and second member 1510. The configuration is such that not only is the clip or suture 52 contained within the combined structures, but the configuration of the first member 1306 and the second member tumor 1510 is such that a cutting or slicing functionality is achieved as they come together. The respective surfaces of the members can be configured to closely align, similar to a pair of scissors, such that the tissue bridge 50 can be cut. The interior structure 1507 and 1511 of the respective first member 1306 and the second member 1510 can be cylindrical in nature, or any other configuration. Step 4 illustrates a last step in the process in which the combined first member 1506 and the second member 1510 as shown as feature 1512 within the combined structure 1512 as the clip or suture 52. The combined structure 1512 can then be rotated back down into the instrument 1502 via use of the elbow 1508. As is shown at the bottom of step 4, the feature 1514 represents the cut tissue bridge 50 with the absence of the clip or suture 52. The top view of the instrument 1504 is shown as the instrument is retrieved from the valve orifice 74B.

This disclosure notes that the particular positions of elbows within the instrument 1504 can vary. For example, rather than member 1506 rotating down, a member could rotate up with an elbow position near the distal end of member 1504. Thus, there are a variety of mechanical structures which could ultimately yield two members on either side of the bridge 50 and clips 52. All of these variations are considered as within the scope of this disclosure. In general, the instrument is utilized to be able to be inserted into an orifice and then extended or deployed such that the members can surround the bridge and the clips and both cut the bridge and gather the clips in one motion. The resulting structure is shown in step 4 of FIG. 15.

One aspect of this disclosure is to use electromagnetic energy for the cutting operation. This could be ultrasound, radio frequency (RF) or any other appropriate signal that can cut the tissue. The cutting operation can be achieved through sharp edges such as scissor like edges configured within the members as part of this disclosure. In another aspect, the members 1510 in 1506 include the ability to emit electromagnetic energy in order to cause the cutting of the bridge 50. In this regard, the instrument 1504 when include an electrical feed and instrumentation, which would enable an electrical or electromagnetic signal or signals to be communicated from the members in such a way as to cut through the bridge 50. The signal can be a laser such as a femtosecond laser or a picosecond laser, or any laser at an appropriate frequency used for cutting this material. The benefit of using a laser or electromagnetic signal is that there is no need for the members to come together in a cutting motion. Instrumentality can be built into the instrument 1504, such as a video camera and a directionally controllable laser such that a surgeon can view the bridge 50 and direct a cutting laser in the proper position. In another aspect, the instrument 1504 can include feedback mechanisms, such that the laser can be automatically positioned and angled so as to avoid, for example, cutting the clips that only cutting the bridge tissue. Electrical feeds from a control unit can be provided to the instrument 1504 to provide power as well as control signals to the mechanical mechanisms which would include an electromagnetic signal and meter, such as a laser, laser control or positioning mechanisms, feedback, cameras, and so forth.

Once the cutting is achieved, the members 1506 and 1510 our configured to envelop the tissue and the clips 52 such that the combined member structure 1512 can be rotated back to an internal portion of the instrument 1504 for easy retrieval.

Figure 16:
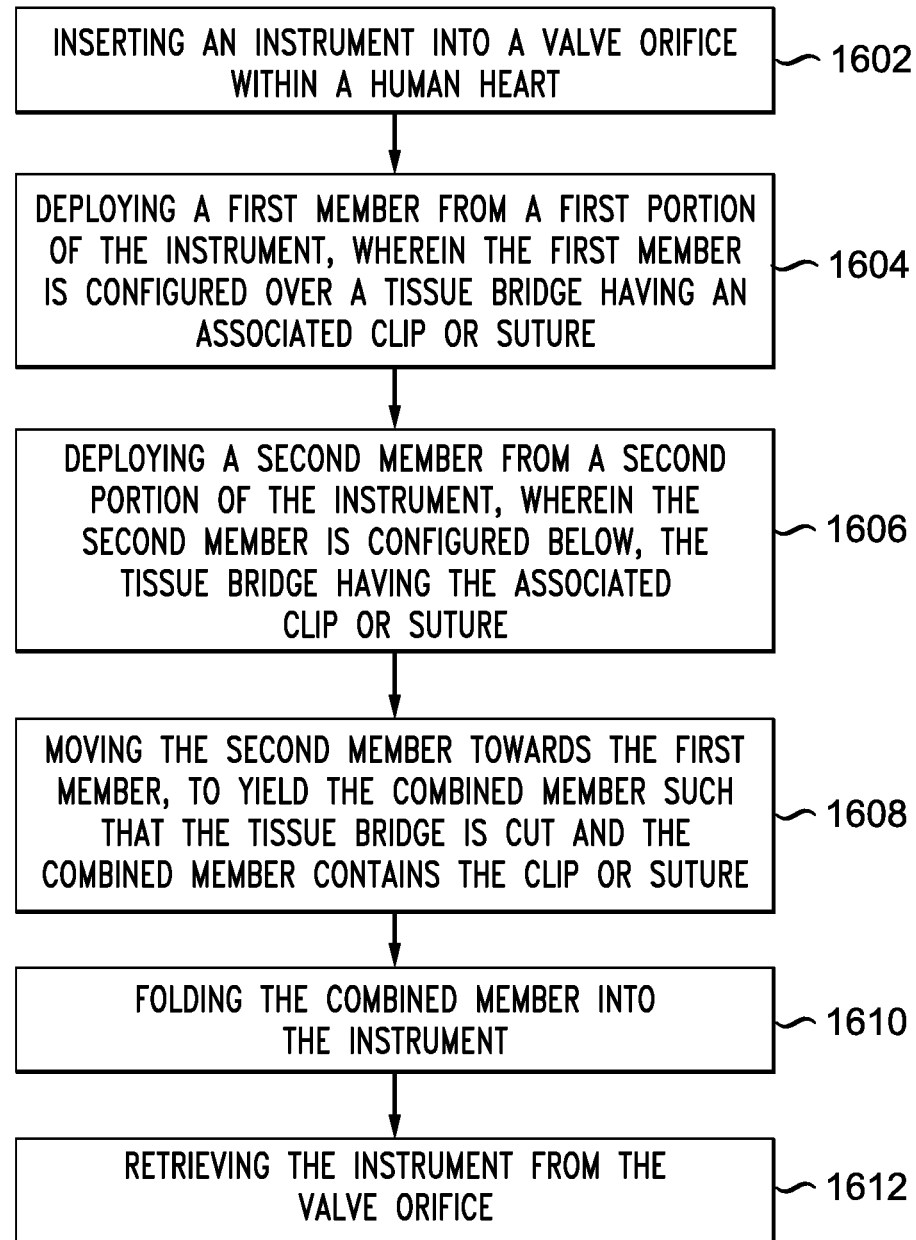
FIG. 16 illustrates a method embodiment.

FIG. 16 illustrates a method aspect that is associated with FIG. 15. The method includes inserting an instrument into a valve orifice within a human heart (1602), deploying a first member from a first portion of the instrument, wherein the first member is configured over a tissue bridge having an associated clip or suture (1604), deploying a second member from a second portion of the instrument, wherein the second member is configured below the tissue bridge having the associated clip or suture (1606), moving the second member towards the first member, to yield the combined member such that the tissue bridge is cut and the combined member contains the clip or suture (1608), folding the combined member into the instrument (1610) and retrieving the instrument from the valve orifice (1612).

It is noted that the first portion of the instruments can be at a distal end of the instrument and the second portion of the instrument can be a portion of the instrument adjacent to the distal end of the instrument. The first member and the second member can have complementary hollow interior configurations such that the first member can receive and envelop the second member, to yield the combined member, and wherein the complementary configurations have sharp edges that slide past each other such that the creation or generation of the combined member correspondingly cuts the tissue bridge 50 as the first member combines with the second member.

Various mechanisms are included to enable the movement of the members as described above, as well as to control such movement. Generally, in step 1 of FIG. 15, feature 1508 represents the technology within the instrument 1502 that enables the first member 1506 to be rotated into the first position, as shown in step 2. The technology within elbow 1508 also includes the ability to receive the second member 1510 into the first member 1506 and then rotate the combined members 1512 back into the instrument 1502 as is shown in step 4.

Feature 1512, in step 1 represents the mechanism necessary to rotate member 1510 down from being configured within the instrument 1502 and into the position shown in step 2. Furthermore, the structure 1513 within the instrument 1502 between the position of member 1506 and member 1510 shown in step 2 enables a sliding of the second member 1510 from its first position to being inserted or enveloped into the first member 1506.

Cutting the tissue bridge can occur via an interaction between edges of the first member and the second member or via an electromagnetic signal emitted from one of the first member or the second member. In one aspect, the combine member includes a cylindrical shaped member containing the associated clip or suture. The combined member can include another shape as well. The method can include cutting the tissue bridge prior to folder the combined member into the instrument and/or controlling a position of an emitter of an electromagnetic signal prior to cutting the tissue bridge. At least one of the first member and the second member can include an electromagnetic signal emitter used for cutting the tissue bridge. Where both members have an emitter, the tissue bridge can be cut from different sides.

An instrument embodiment includes an elongated shaft and a first member configured in the elongated shaft such that the first member can be deployed from a first portion of the instrument, wherein the first member, when deployed, is configured over a tissue bridge within a heart, the tissue bridge having a clip or suture. The instrument further includes a second member configured in the elongated shaft such that the second member can be deployed from a second portion of the elongated shaft, wherein the second member, when deployed, is configured under the tissue bridge within the heart and the clip or suture, wherein the elongated shaft is configured such that the second member, when deployed, can move towards the first member, when deployed, to yield a combined member which receives the tissue bridge and the clip or suture, wherein the elongated shaft receives the combined member.

When the second member moves towards the first member, a cutting of the tissue bridge occurs via an interaction between edges of the first member and the second member. Cutting the tissue bridge can occur via an electromagnetic signal emitted from one of the first member or the second member, or both. Cutting the tissue bridge will typically occur prior to folding the combined member into the elongated shaft or as part of the folding process. The instrument can include a controller that controls a position of an emitter of an electromagnetic signal prior to cutting the tissue bridge. The electromagnetic signal emitter further can include a directional controller which controls a direction of the electromagnetic signal emitter. This enables the user to point the emitter to a proper location for cutting the tissue bridge.

The instrument can also include a controller in communication with the electromagnetic signal emitter that enables a user to directionally control the electromagnetic signal emitter via the directional controller.

From the foregoing, it will be appreciated that, although specific embodiments have been described herein for purposes of illustration, various modifications or variations may be made without deviating from the spirit or scope of inventive features claimed herein. For example, various elements disclosed herein relative to one embodiment may be usable with one or more additional embodiments, including in some cases interchangeability of the respective parts. Other embodiments will be apparent to those skilled in the art from consideration of the specification and figures and practice of the arrangements disclosed herein. It is intended that the specification and disclosed examples be considered as exemplary only, with a true inventive scope and spirit being indicated by the following claims and their equivalents.

I claim:

1. An apparatus for excising and removing a clip or suture joining leaflets of a native heart valve, the apparatus comprising:
   an elongate shaft configured for remote access to a native heart valve, the elongate shaft having a proximal end, a distal end, and a lumen defined therein;
   a clamp at the distal end of the elongate shaft, the clamp configured to receive a clip or suture joining native leaflet tissue, the clamp including a passageway extending along a length thereof in communication with the lumen; and
   a cutter moveable within the passageway to encompass a clip or suture joining native leaflet tissue received within the clamp and cut native leaflet tissue configured to proximate the clip or suture.

2. The apparatus of claim 1, wherein the cutter is configured to excise a clip or suture joining native leaflet tissue from the native leaflet tissue.

3. The apparatus of claim 2, wherein the cutter is moveable towards a distal end of the clamp to excise a clip or suture joining native leaflet tissue from the native leaflet tissue, and further wherein the cutter is moveable within the lumen towards a proximal end of the elongate shaft with the excised clip or suture.

4. The apparatus of claim 2, wherein the cutter is configured to contain an excised clip or suture.

5. The apparatus of claim 1, wherein the clamp is configured to be inserted through an orifice defined by native leaflet tissue adjacent a clip or suture joining native leaflet tissue.

6. The apparatus of claim 1, wherein the cutter is a hollow cylinder having a cutter distal end defining a cutting edge.

7. The apparatus of claim 6, wherein the cutting edge is serrated.

8. The apparatus of claim 1, wherein the cutter resembles a biopsy punch.

9. The apparatus of claim 1, wherein the cutter is rotatable about a longitudinal axis.

10. The apparatus of claim 1, wherein the cutter is coupled with an actuator extending from the proximal end of the elongate shaft.

11. The apparatus of claim 1, wherein the cutter includes at least one of a radio-frequency or ultrasonic cutter.

12. A method for excising and removing a clip or suture joining leaflets of a native heart valve, the method comprising:
   delivering to a native heart valve an apparatus for excising and removing a clip or suture joining native leaflet tissue, the apparatus including:
      an elongate shaft configured for remote access to a native heart valve, the elongate shaft having a proximal end, a distal end, and a lumen defined therein;
      a clamp at the distal end of the elongate shaft, the clamp configured to receive a clip or suture joining native leaflet tissue, the clamp including a passageway extending along a length thereof in communication with the lumen; and
      a cutter moveable within the passageway;
   positioning the apparatus at the native heart valve with a clip or suture joining native leaflet tissue received in the clamp; and
   moving the cutter within the passageway to encompass the clip or suture joining native leaflet tissue received in the clamp and cut native leaflet tissue proximate the clip or suture.

13. The method of claim 12, wherein moving the cutter within the passageway to encompass the clip or suture joining native leaflet tissue includes excising the clip or suture from the native leaflet tissue.

14. The method of claim 13, wherein the lumen is sized to receive a clip or suture from the passageway, and wherein moving the cutter includes moving the cutter and excised clip or suture within the lumen towards the proximal end of the elongate shaft after excising the clip or suture.

15. The method of claim 12, wherein the apparatus is delivered percutaneously.

16. The method of claim 12, wherein the apparatus is delivered transapically.

17. The method of claim 12, wherein the apparatus is delivered transatrially.

18. The method of claim 12, wherein the native heart valve is a mitral valve.

19. The method of claim 12, wherein positioning the apparatus at the native heart valve includes positioning the clamp through an orifice defined by native leaflet tissue adjacent the clip or suture joining native leaflet tissue.

20. The method of claim 19, wherein positioning the apparatus includes cutting through tissue or debris obstructing the orifice.

21. The method of claim 12, wherein moving the cutter includes rotating the cutter about a longitudinal axis.

* * * * *